United States Patent
Takaishi

(10) Patent No.: US 8,320,654 B2
(45) Date of Patent: Nov. 27, 2012

(54) BONE MINERAL DENSITY EVALUATION DEVICE AND BONE MINERAL DENSITY EVALUATION METHOD

(76) Inventor: Yoshitomo Takaishi, Himeji (JP)

( * ) Notice: Subject to any disclaimer, the term of this patent is extended or adjusted under 35 U.S.C. 154(b) by 1048 days.

(21) Appl. No.: 10/565,863

(22) PCT Filed: Jul. 29, 2004

(86) PCT No.: PCT/JP2004/010815
§ 371 (c)(1),
(2), (4) Date: Jan. 24, 2006

(87) PCT Pub. No.: WO2005/011497
PCT Pub. Date: Feb. 10, 2005

(65) Prior Publication Data
US 2007/0025607 A1   Feb. 1, 2007

(30) Foreign Application Priority Data

Jul. 31, 2003 (JP) .................. 2003-283686
Jun. 23, 2004 (JP) .................. 2004-185372

(51) Int. Cl.
*G06K 9/00* (2006.01)
(52) U.S. Cl. ............. 382/132; 433/27; 433/33; 378/28; 378/38; 378/63; 378/90; 702/8
(58) Field of Classification Search .............. 382/132, 382/168
See application file for complete search history.

(56) References Cited

U.S. PATENT DOCUMENTS

| | | | |
|---|---|---|---|
| 5,068,788 A * | 11/1991 | Goodenough et al. | 382/131 |
| 5,335,260 A | 8/1994 | Arnold | |
| 5,544,258 A * | 8/1996 | Levien | 382/169 |
| 5,892,808 A * | 4/1999 | Goulding et al. | 378/63 |
| 5,974,166 A * | 10/1999 | Ino et al. | 382/132 |
| 6,078,686 A * | 6/2000 | Kim | 382/167 |

(Continued)

FOREIGN PATENT DOCUMENTS

EP   0411155 A1   2/1991

(Continued)

OTHER PUBLICATIONS

Choel, "Trabecular alveolar bone in the human mandible: a dual-energy x-ray absorptiometry study," Mar. 2003, Oral Surgery, oral medicine, oral pathology, oral radiology, and endodontics, vol. 95, pp. 364-370.*

Office Action issued in priority application (Japanese Application No. 2004-185372).

International Search Report from PCT/JP2004/010815 dated Oct. 5, 2004.

(Continued)

*Primary Examiner* — John Lee
(74) *Attorney, Agent, or Firm* — Duane Morris LLP

(57) ABSTRACT

To evaluate an exact bone mineral density, when a reference bar region in an X-ray picture of a mandible and a reference bar disposed beside the mandible is selected, the mean value and deviation of the brightness of this region are displayed by means of letter groups. When an evaluation object region is selected, the brightness of this region is corrected according to the mean value and deviation of the brightness of the reference bar region and standard mean value and deviation, or, in other words, according to a fixed reference. The corrected brightness is displayed in the form of histogram. Furthermore, the mean value and deviation of the corrected brightness are determined, and they are displayed by means of letter groups. The bone mineral density is quantitatively evaluated from the histogram and the mean value and deviation of the corrected brightness.

14 Claims, 40 Drawing Sheets

U.S. PATENT DOCUMENTS

| | | | |
|---|---|---|---|
| 6,093,019 A * | 7/2000 | Morandi et al. | 433/29 |
| 6,261,248 B1 * | 7/2001 | Takaishi et al. | 600/590 |
| 6,296,387 B1 * | 10/2001 | Guillemaud | 378/207 |
| 6,320,931 B1 | 11/2001 | Arnold | |
| 6,819,794 B2 * | 11/2004 | Inoue | 382/169 |
| 2001/0021269 A1 * | 9/2001 | Inoue | 382/169 |
| 2002/0114425 A1 | 8/2002 | Lang et al. | |
| 2003/0063704 A1 | 4/2003 | Lang | |
| 2003/0112921 A1 * | 6/2003 | Lang et al. | 378/54 |
| 2004/0151375 A1 * | 8/2004 | Kim et al. | 382/181 |

FOREIGN PATENT DOCUMENTS

| | | |
|---|---|---|
| JP | 62-266053 A * | 11/1987 |
| JP | 63-030945 | 8/1989 |
| JP | 3-215256 A | 9/1991 |
| JP | 7-148143 A | 6/1995 |
| JP | 01243464 | 9/2001 |
| WO | 0230283 A2 | 4/2002 |
| WO | WO-02/30283 * | 4/2002 |

OTHER PUBLICATIONS

European Communication—Supplementary European Search Report dated May 18, 2009, Application No./Patent No. 04771028.0-1265/1649809 PCT/JP2004010815.

"Geometric and Densitometric Standardization of Intraoral Radiography Through Use of a Modified XCP System," Oral Surgery Oral Medicine Oral Pathology, vol. 87, No. 2, Feb. 1999, Thomas E. Southard, DDS, MS, Dawn M. Wunderle, BS, Karin A. Southard, DDS, MS and Jane R. Jakobsen, BS, MA, Iowa City, Iowa, University of Iowa (Copyright © 1999).

"Digital Image Processing," Clinical Oral Implants Research, Copyright Munksgaard 1994, ISSN 0905-7161, I. Fourmousis, U. Brägger, W. Bürgin, M. Tonetti, N. P. Lang, Department of Periodontology and Fixed Prosthodontics, University of Berne School of Dental Medicine, Switzerland.

* cited by examiner (a) Front View (b) Side View

300

| ITEM | Picture 1 | Picture 2 | Picture 3 | Picture 4 |
|---|---|---|---|---|
| Hb[x] | | | | |
| Mb | (SMb) | | | |
| Db | (SDb) | | | |
| Ho[x] | | | | |
| Mo | | | | |
| Do | | | | |
| Ho'[x] | | | | |
| Mo' | | | | |
| Do' | | | | |

FIG.12

| No. | Age [Year] | BMD Value [gms/cm²] | T Value [%] | Mean Brightness Mo' |
|---|---|---|---|---|
| 1 | 50 | 1.071 | 106 | 99.99 |
| 2 | 51 | 0.702 | 69 | 63.03 |
| 3 | 51 | 0.923 | 91 | 96.14 |
| 4 | 52 | 1.323 | 131 | 119.02 |
| 5 | 54 | 0.924 | 91 | 83.54 |
| 6 | 54 | 0.948 | 94 | 104.05 |
| 7 | 55 | 0.747 | 74 | 95.53 |
| 8 | 55 | 0.929 | 92 | 98.68 |
| 9 | 56 | 1.021 | 101 | 113.93 |
| 10 | 56 | 0.887 | 88 | 88.92 |
| 11 | 56 | 1.049 | 104 | 146.36 |
| 12 | 56 | 1.076 | 106 | 99.73 |
| 13 | 58 | 0.927 | 92 | 92.51 |
| 14 | 58 | 0.711 | 70 | 80.53 |
| 15 | 59 | 0.812 | 80 | 73.81 |
| 16 | 59 | 0.995 | 98 | 76.42 |
| 17 | 59 | 0.814 | 81 | 70.16 |
| 18 | 60 | 0.910 | 90 | 83.55 |
| 19 | 60 | 0.789 | 79 | 81.66 |
| 20 | 60 | 0.826 | 82 | 95.09 |
| 21 | 60 | 0.980 | 97 | 95.37 |
| 22 | 61 | 0.692 | 68 | 80.20 |
| 23 | 62 | 0.729 | 72 | 78.35 |
| 24 | 62 | 0.993 | 98 | 64.88 |
| 25 | 62 | 1.006 | 99 | 82.10 |
| 26 | 63 | 0.813 | 80 | 94.69 |
| 27 | 64 | 0.707 | 70 | 72.73 |
| 28 | 65 | 0.675 | 67 | 58.85 |
| 29 | 65 | 0.592 | 59 | 88.14 |
| 30 | 66 | 0.842 | 83 | 96.11 |
| 31 | 66 | 0.683 | 68 | 75.54 |
| 32 | 67 | 0.527 | 52 | 52.28 |
| 33 | 68 | 0.792 | 78 | 80.07 |
| 34 | 69 | 0.715 | 71 | 77.68 |
| 35 | 69 | 0.780 | 77 | 97.32 |
| Average | 59.66 | 0.855 | 84.51 | 87.34 |
| Coefficient of Correlation to Mo' | | 0.6439 | 0.6481 | — |

FIG.22

| T Value [%] | Mean Brightness Mo' |
|---|---|
| 70 or less | 71.41 |
| 71 ~ 80 | 84.89 |
| 81 ~ 99 | 87.68 |
| 100 or more | 115.81 |

| ITEM | Picture 1 | Picture 2 | Picture 3 | Picture 4 |
|---|---|---|---|---|
| Hb[x] | ✗ | | | |
| Mb | ✗ | | | |
| Db | ✗ | | | |
| Ybmax | | ✗ | ✗ | ✗ |
| Ybmin | | ✗ | ✗ | ✗ |
| Ysmax | | ✗ | ✗ | ✗ |
| Ysmin | | ✗ | ✗ | ✗ |
| Ha'[x] | | | | |
| Hb'[x] | | | | |
| Mb' | (SMb) | | | |
| Db' | (SDb) | | | |
| Ho'[x] | | | | |
| Mo' | | | | |
| Do' | | | | |

FIG.29 and a picture of the specimen are taken, being juxtaposed on a single X-ray film. The density, i.e. darkness or lightness, of the specimen picture is detected by the detecting means, and the density of the X-ray picture or, more specifically, density of the picture of the mandible, is modified by the modifying means in such a manner that the result of detection by the detecting means matches a reference value. Based on the density modified by the modifying means, the evaluating means evaluates the bone mineral density of the mandible and, hence, the skeletal bone mineral density. In other words, the density of the picture of a given specimen is modified to match the reference value, so that the density of the picture on the X-ray film is modified with reference to the constant reference value, from which the bone mineral density is evaluated.

BONE MINERAL DENSITY EVALUATION DEVICE AND BONE MINERAL DENSITY EVALUATION METHOD

TECHNICAL FIELD

This invention relates to a system for evaluating a bone mineral density and a method of evaluating a bone mineral density, and, more particularly, to a system and method for evaluating a bone mineral density, using an X-ray picture of, for example, a mandible.

BACKGROUND

Recently, study on using a bone mineral density of a mandible to evaluate a skeletal bone mineral density of a whole body of a person has attracted attention. A non-patent literature 1 below reports that the bone mineral density of a dental alveolus of a mandible, or, more particularly, the bone mineral density at a location between premolars (or between the first and second premolars) and away by about 6 mm from the neck (the junction between the enamel and cementum portions) toward the apex is closely related to the skeletal bone mineral density of a person. It also shows experiments for evaluating the bone mineral density of an alveolus from a density of a radiograph of the alveolus, and, then, estimating the skeletal bone mineral density from the evaluation of the alveolar bone mineral density.

Non-Patent Literature 1: Grethe Jonasson, Gudrun Bankvall, Stavros Kiliaridis: Estimation of skeletal bone density by means of trabecular pattern of the alveolar bone, its interdental thickness, and the bone mass of the mandible; "ORAL SURGERY ORAL MEDICINE ORAL PATHOLOGY" September 2001, Volume 92, Number 3, p. 346-p.352.

DESCRIPTION OF THE INVENTION

Problem to be Solved by the Invention

The technique disclosed in the literature 1, however, is still at the level of study, and only shows that the skeletal bone mineral density of a person can be evaluated, using human senses, from density on a radiograph of a dental alveolar bone. In fact, the previous technique was not able to provide accurate evaluation of the skeletal bone mineral density, because a density of radiographs varies, depending on various conditions occurring, for example, when the radiographs are taken, and when they are developed and kept, (specifically, the time period spent when radiographs are taken, the temperature of developing solutions, environments in which the radiographs are kept, for example). Thus, the reference to be used in evaluating a bone mineral density had to be changed for individual radiographs.

Therefore, an object of the present invention is to provide a practical bone mineral density evaluation system and method.

Means to Solve the Problem

A bone mineral density evaluation system according to the present invention is used to evaluate a bone mineral density from an X-ray picture of a mandible. An X-ray picture of a specimen disposed beside the mandible is also used. The system includes detecting means for detecting a density of the specimen picture, modifying means for modifying the density of the X-ray picture of the mandible in such a manner that the detection result obtained by the detecting means matches the reference value, and evaluating means for evaluating the bone mineral density from the density as modified by the modifying means.

According to the present invention, a picture of a mandible and a picture of the specimen are taken, being juxtaposed on a single X-ray film. The density, i.e. darkness or lightness, of the specimen picture is detected by the detecting means, and the density of the X-ray picture or, more specifically, density of the picture of the mandible, is modified by the modifying means in such a manner that the result of detection by the detecting means matches a reference value. Based on the density modified by the modifying means, the evaluating means evaluates the bone mineral density of the mandible and, hence, the skeletal bone mineral density. In other words, the density of the picture of a given specimen is modified to match the reference value, so that the density of the picture on the X-ray film is modified with reference to the constant reference value, from which the bone mineral density is evaluated.

The evaluating means may evaluate the bone mineral density based on the modified density of a particular region of an X-ray picture.

In this case, the particular region preferably includes a region corresponding to the portion of the alveolar bone around the first premolar.

The detecting means may determine the density of a given portion of the picture of the specimen, for example, the darkest or lightest portion of the picture of the specimen. In other words, the density of the X-ray picture may be modified in such a manner that the darkness or lightness of the given portion can match the reference value.

The density of the specimen may vary from portion to portion when, for example, the thickness of the specimen is not uniform. In such case, the detecting means may preferably be arranged to detect the mean value or variation of the density of the specimen. Then, the density of the X-ray picture is modified in such a manner that the mean value or deviation of the density of the picture of the specimen matches the reference value.

Setting means for setting a desired value as the reference value may be provided.

The reference value may be set based on a result of detection by the detecting means of a given X-ray picture. The density of another X-ray picture can be modified with reference to the density of the given X-ray picture. The density of the said another X-ray picture is adjusted to match the density of the given X-ray picture.

The evaluating means may be provided with display means for displaying the corrected density by means of a histogram.

The evaluating means may be provided with judgment means for judging, from the density after modification, the level of the bone mineral density, or, for example, whether the bone mineral density is normal or should be improved.

The system may be provided with output means for outputting together a plurality of results of evaluation of a plurality of X-ray pictures provided by the evaluating means. Such arrangement is very useful for grasping change with time of the bone mineral density.

A bone mineral density evaluating method according to the present invention is to evaluate bone mineral density from an X-ray picture of a mandible. The X-ray picture includes a picture of a specimen juxtaposed with the mandible. The method includes steps of detecting the density of the picture of the specimen, modifying the density of the picture based on the detection results, and evaluating the bone mineral density based on the density as modified in the modifying step.

BRIEF DESCRIPTION OF THE DRAWINGS

FIG. 12 is a schematic illustration of a table used in the bone mineral density evaluating system of FIG. 1.

FIG. 22 is a table showing corrected brightness values, actual BMD values and T values obtained by the bone mineral density evaluating system.

FIG. 23 shows T value zones shown in FIG. 22 and mean values of corrected brightness values for the respective zones.

FIG. 29 is a schematic illustration of a table different from the one shown in FIG. 12.

BEST MODE FOR EMBODYING THE INVENTION

Now, a bone mineral density evaluation system for dental use according to a first embodiment is described with reference to FIGS. 1-21.

Figure 1:
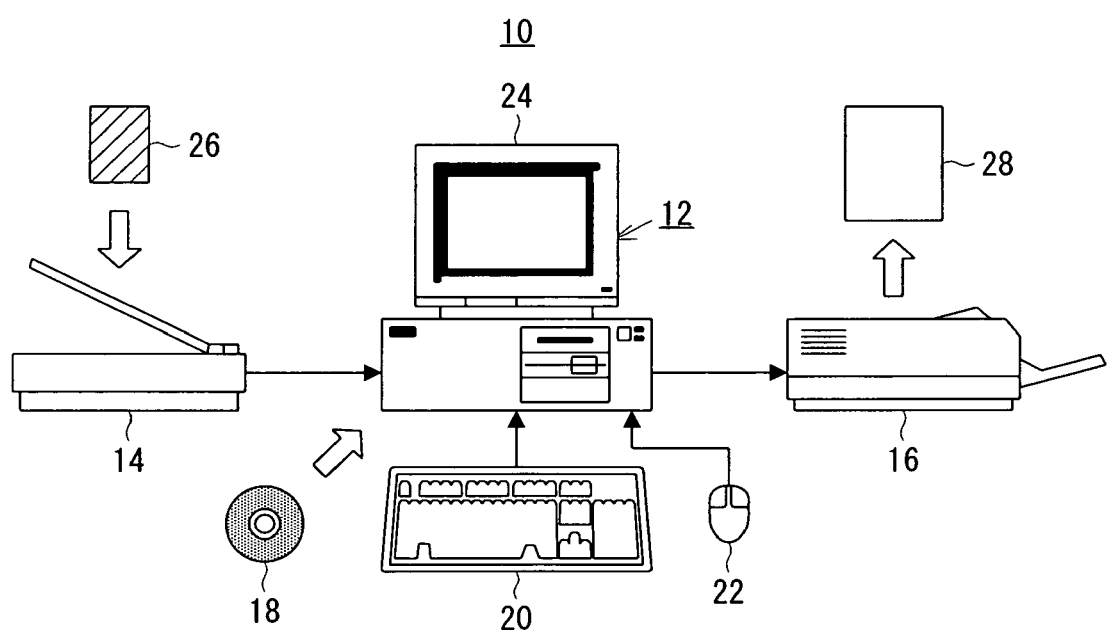
FIG. 1 is an overall configuration of a bone mineral density evaluating system according to a first embodiment of the present invention.

As shown in FIG. 1, the bone mineral evaluation system 10 according to the first embodiment includes a personal computer (hereinafter referred to as PC) 12. The PC 12 has a bone mineral density evaluation program installed from a CD-ROM (Compact Disc ROM) 18. Upon boot-up of the bone mineral density program, the PC 12 functions as a bone mineral density evaluating apparatus. A film scanner 14 functioning as picture input means and a laser printer 16 functioning as printing means are connected to the PC 12. The PC 12 is further provided with a keyboard 20 and a mouse 22 functioning as command input means and a display 24 functioning as display means.

In the bone mineral density evaluation system with the above-described arrangement, an picture of a mandible taken on an X-ray film 6 is read by the film scanner 14 and converted into digital picture data. The converted picture data is inputted to the PC 12 and written in a hard disc (not shown) in the PC 12 in, for example, an eight (8) bit or twenty-four (24) bit bitmap format. In this manner, plural pieces of picture data of the same position (mandible) of the same patient taken on different days are successively recorded on the hard disc.

Figure 2:
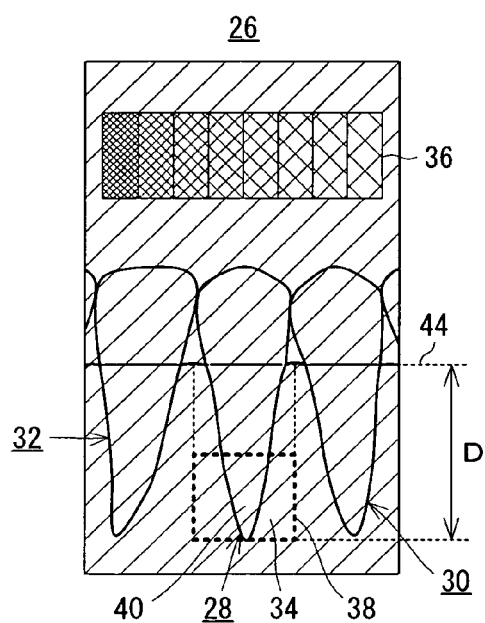
FIG. 2 is an illustration of an example of an X-ray film on which a picture has been taken by the bone mineral density evaluating system of FIG. 1.

The X-ray film 26 contains therein a picture of a portion of a mandible about a first premolar, and, more particularly, as shown in FIG. 2, a first premolar 28, a canine 30 and a second premolar 32 adjacent to the first premolar 28, and an alveolar bone 34 supporting the teeth 28, 30 and 32. A reference bar 36, described later, is taken, being juxtaposed with or, for example, above the teeth 28-32 (or more exactly, the picture of the teeth 28-32).

The PC 12 evaluates the bone mineral density (the bone mineral quantity) of the alveolar bone 34 around the lower half of the root 40 of the first premolar 28 from the picture data of the mandible, or, more specifically, the density of the picture of the lower half of the root 40 of the first premolar 28 and the alveolar bone 34 in a broken line box 38 in FIG. 2, and, hence, the skeletal bone mineral density of the patient. When the picture has a lower density (i.e. the picture is lighter), for example, an evaluation that the alveolar bone has a higher bone mineral density is given, and if the picture has a higher density (i.e. the picture is dark), an evaluation that the alveolar bone has a lower bone mineral density is given. The result of evaluation is displayed on the display 24. The evaluation result also may be recorded on the hard disc, if necessary, and may be printed by the laser printer 24 on the patient's medical record 42 (or a paper sheet to be put in the record).

The reason why the object of the evaluation is the lower half of the root 40 of the first premolar 28 and the alveolar bone 34 around it is that the bone mineral density of the alveolar bone 34 around the first premolar 28 (i.e. the alveolar bone between the first and second premolars) closely correlates to the skeletal bone mineral density of a person, as described in the previously mentioned publication. The upper portion of the alveolar bone 34 (or the root 40) is not evaluated for the reason that it tends to be affected by periodontal disease so that, if it is affected by periodontal disease, its bone mineral density decreases. The component of the tooth root 40 itself (i.e. the density of its picture) has no special relationship with the skeletal bone mineral density of a person, and, therefore, it can be neglected in evaluation. The component of the root 40 is almost invariable, and, therefore, whether it is taken into account or not does not influence the evaluation result. In the first embodiment, therefore, the lower portion of the root 40 is also an object of evaluation.

Here, the objects to be evaluated are specifically described. The upper edge of the rectangular region within the broken line square 38 subjected to the evaluation is at the midpoint of the distance D between the neck and the apex of the first premolar 28, and the lower edge of the rectangular region 38 is at the apex of the first premolar 28. The right-side edge of the rectangular region 38 passes the midpoint between the first premolar 28 and the canine 30 on a line 44 connecting the necks of the teeth 28, 30 and 32. Similarly, the left edge of the region 38 is at the midpoint between the first premolar 28 and the second premolar on the line 44.

Figure 3:
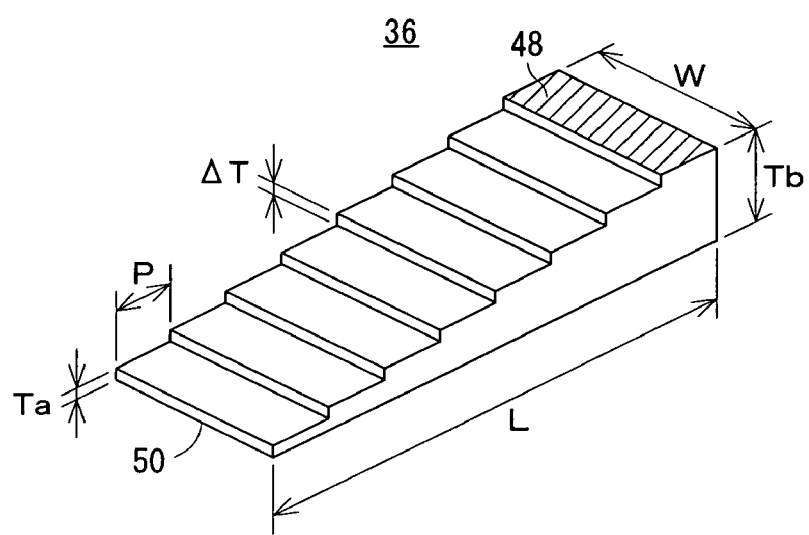
FIG. 3 is a schematic perspective view of an aluminum block to be attached to the X-ray film of FIG. 2.

The above-mentioned reference bar 36 is a picture resulting from photographing an aluminum block as the specimen, shown in FIG. 3. Hereinafter, the aluminum block is also denoted by a reference numeral "36". The aluminum block 36 is staircase-shaped, whose thickness changes in step in the length direction. The step difference ΔT and the spacing P between adjacent steps (i.e. the width of each tread) are constant. The number of the steps is, for example, from seven to nine. A piece of aluminum foil 48 is bonded to the upper surface of the uppermost step in order to block an X-ray 46, which is described later. The length L of the aluminum block 36 is about 20 mm, and the width W is about 10 mm. The thickness Ta at the lowermost step (i.e. the distance between the bottom surface 50 and the upper surface of the lowermost step) is about 1 mm. The thickness Tb at the uppermost step (i.e. the distance between the bottom surface 50 and the upper surface of the uppermost step) is from about 6 mm to 8 mm, for example.

Figure 4:
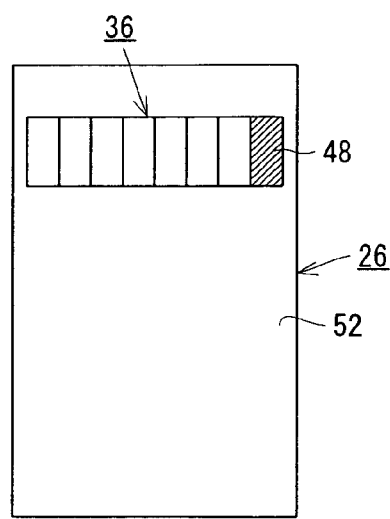
FIG. 4 is an illustration of an example of an X-ray film before a picture is taken by the bone mineral density evaluating system of FIG. 1.
Figure 4:
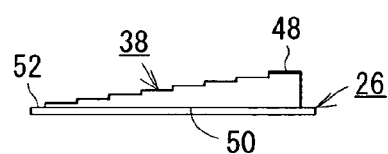
Figure 5:
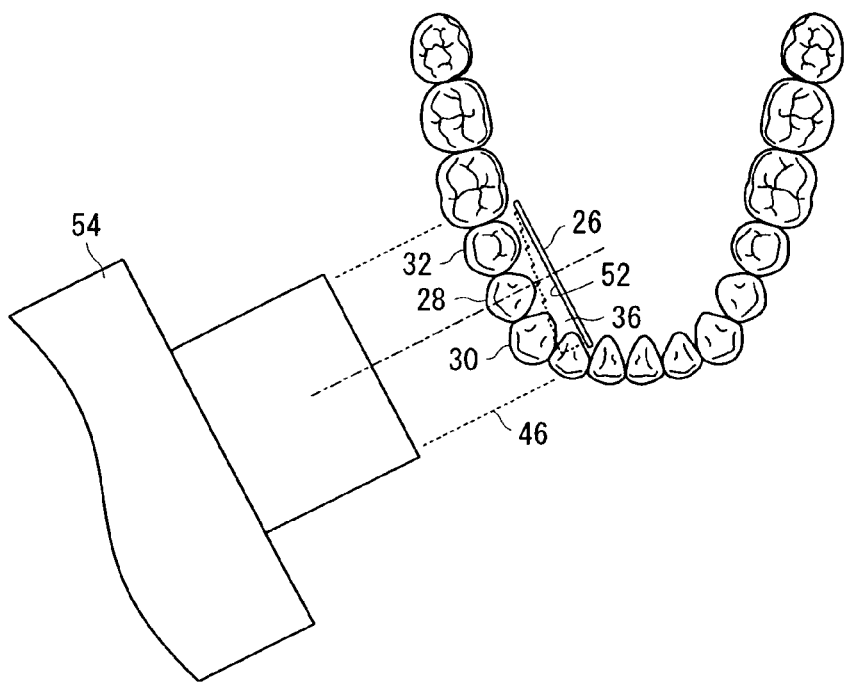
FIG. 5 illustrates how an X-ray picture is taken, using the film shown in FIG. 4.

Before taking a picture, the aluminum block 36 is stuck to a photograph surface (or a surface to be exposed to an X-ray) 52 of a vertically elongated rectangular X-ray film 26 as shown in FIG. 4. More specifically, the aluminum block 36 is stuck to an upper portion of the X-ray film 26, with its longer edge extending along with the upper edge of the film 26 and with the bottom surface 50 facing the surface 52 of the film 26. When a picture of a mandible is taken, the X-ray film 26 with the aluminum block 36 stuck on it is placed inward of the teeth 28-32 to be X-rayed, as shown in FIG. 5, with the upper edge of the film 26 (along which the block 36 extends) facing the upper jaw of the patient (not shown), and with the photograph surface 52 facing outward. The X-ray film 26 is held by means of a film holder (not shown). An X-ray camera (or X-ray radiator) 54 disposed outside the object (i.e. the teeth 28-32 and the alveolar 34) projects X-rays 46 toward the photograph surface 52 of the X-ray film 26. This produces, on the single X-ray film 26, a picture of the teeth 28-32, a picture of the alveolar bone 34, and a picture of the aluminum block 36 or reference bar 36, as shown in FIG. 2.

As described above, since the aluminum block 36 has a staircase shape, the reference bar 36, which is the X-ray picture of the aluminum block 36, has a density varying along its length corresponding to the thickness or height of each step. Specifically, since a smaller thickness portion has a higher transmissivity to X-rays, the picture is darker, whereas a larger thickness portion has a lower transmissivity to X-rays, so that its picture is lighter. Since the region onto which the aluminum foil piece 48 is stuck hardly allows X-rays to pass therethrough, the corresponding picture is lightest.

Now, let it be assumed that a plurality (four or more in this example) of X-ray pictures of the same patient taken on different days have been stored in the hard disc of the PC 12. When the bone mineral density evaluating program is booted up, a main picture 100 like the one shown in FIG. 6 appears on the display 24 of the PC 12.

The main picture 100 includes a horizontally elongated title bar 102 in its uppermost region. In the title bar 102, a horizontally aligned letter group 104 representing the patient's medical record number are displayed beginning at the left end. Displayed below the title bar 102 is a horizontally elongated menu bar 106 similar to the title bar 102, which contains horizontally aligned letter groups 108, 108, . . . , representing the contents of the menu accessible on the main picture 100. A tool bar 110 is displayed below the menu bar 106, which contains a plurality of horizontally aligned tool buttons 112, 112, . . . , which are designed versions of the contents of the menu. Displayed below the tool bar 110 is a rectangular frame region 114.

In an upper portion of the frame region 114, four, generally square picture boxes 116, 116, . . . , are horizontally aligned. Four letter groups 118, 118, . . . , namely, "Picture 1", "Picture 2", "Picture 3" and "Picture 4", for the pictures to be displayed in the respective picture boxes 116 are displayed below the respective picture boxes 116, being arranged in the named order from left to right. Further, below each of the letter groups 118, two letter groups 120 and 122 are displayed in two rows. The letter groups 120 and 122 are for mean values (MV) Mo' and deviations (Dev.) Do' of corrected luminance Yo' [i, j] shown in a subsidiary picture (dialogue box) 200 described later.

On the right side of the row of the picture boxes 116, four radio buttons 124, 124, . . . , for use in selecting one of the picture boxes 116 to be activated, are vertically arranged. Letter groups 126 indicating "Picture A" ("A" being any of numerals "1" through "4") are displayed on the right side of the respective radio buttons, for which they are used. Above the vertical arrangement of the radio buttons 124, a row of letters "Select Picture" 128, indicating the function of the radio buttons 124, is displayed. Below the vertical arrangement of the radio buttons 124, two letter groups 130 and 132 are displayed, being arranged vertically. The letter groups 130 and 132 are for a standard mean value (SMV) SMb and a standard deviation (SD) SDb, respectively, which are described later.

Displayed below the frame region 114 is a histogram display area 134, which will be described in detail later. Vertical scale lines 136 are displayed at constant intervals along the abscissa in the histogram display area 134, and letter groups 138 for index values are displayed beneath the respective scale lines 136.

Figure 6:
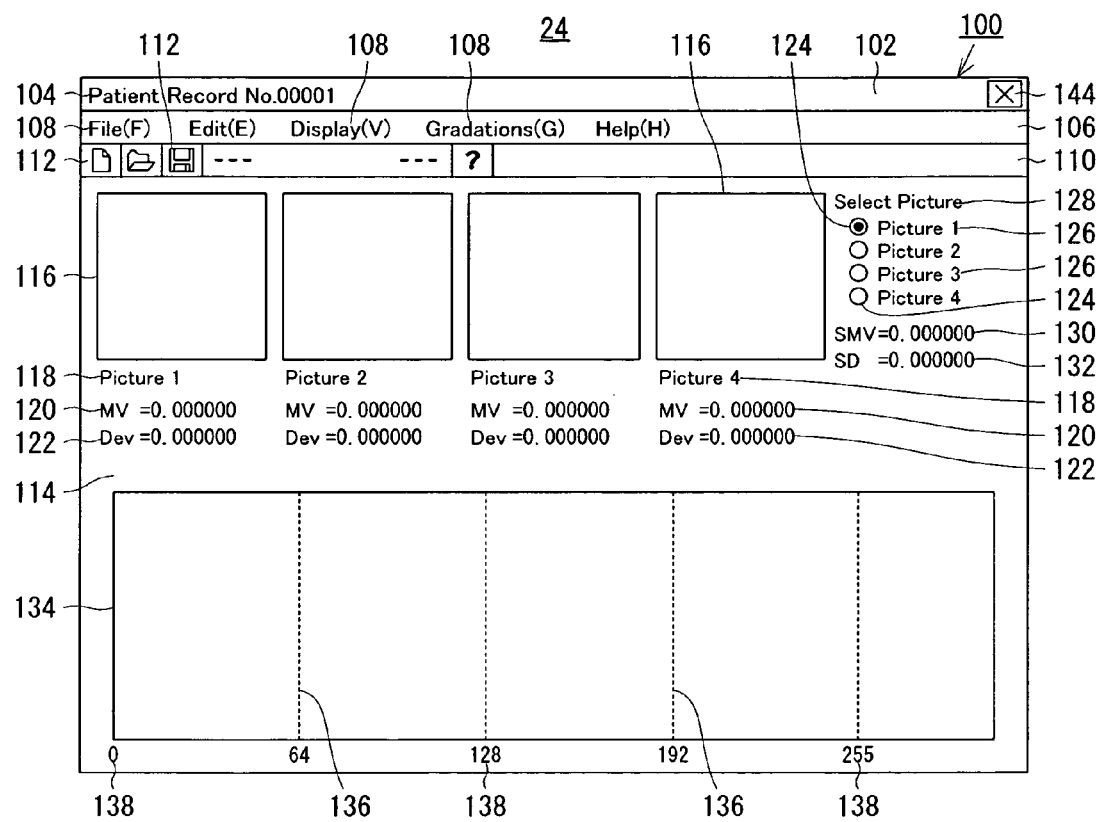
FIG. 6 is an illustration of an example of a main picture displayed on a PC display of the bone mineral density evaluating system of FIG. 1.
Figure 7:
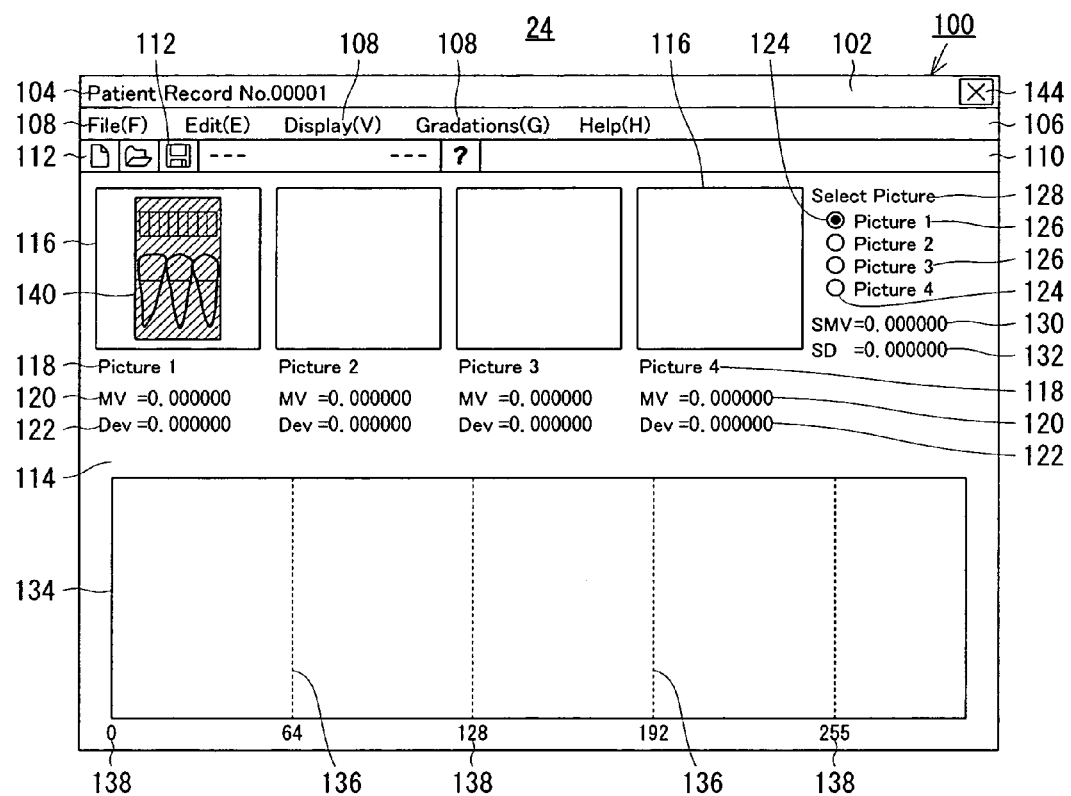
FIG. 7 is an illustration of an example of the main picture different from the one of FIG. 6.
Figure 8:
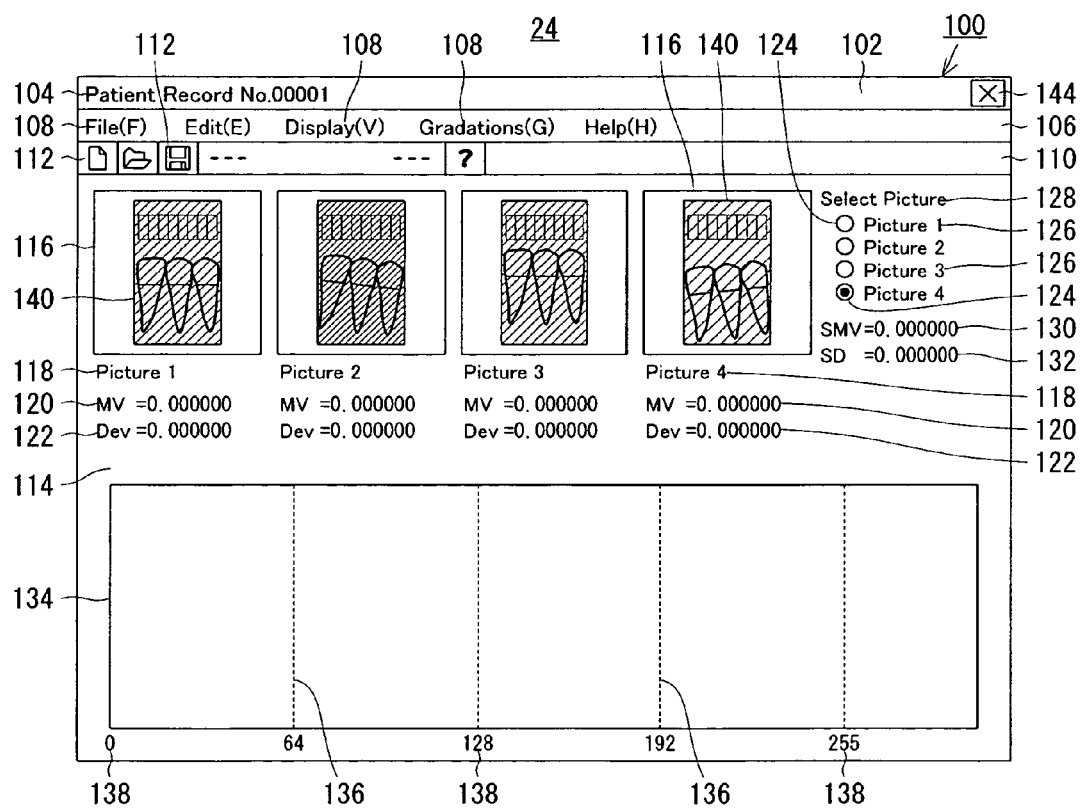
FIG. 8 is an illustration of another example of main picture different from the one shown in FIG. 7.

With the main picture 100 shown in FIG. 6 displayed, the mouse 22 is used to turn on (click) the radio button 124 for "Picture 1", and, the mouse 22 is used again to read in desired picture data from the hard disc. This causes an X-ray picture 140 corresponding to the picture data to be displayed in the picture box 116 for "Picture 1", as shown in FIG. 7. The X-ray picture 140 is displayed in gray scale. If, however, the original picture data is color data, it is converted into gray scale data when it is read in from the hard disc. A command for reading in the picture data is stored in a "File" menu in the menu bar 106.

Similarly, with respect to the other "Picture 2", "Picture 3" and "Picture 4", when picture data corresponding to them are read in by turning the corresponding radio buttons 124 on, X-ray pictures 140 corresponding to the read in picture data are displayed in the corresponding picture boxes 116. The X-ray pictures 140 displayed in the respective picture boxes 116 are of the same person, and the pictures of "Picture 1", "Picture 2", "Picture 3" and "Picture 4" were older in the named order, with the picture of "Picture 1" being the oldest.

Figure 9:
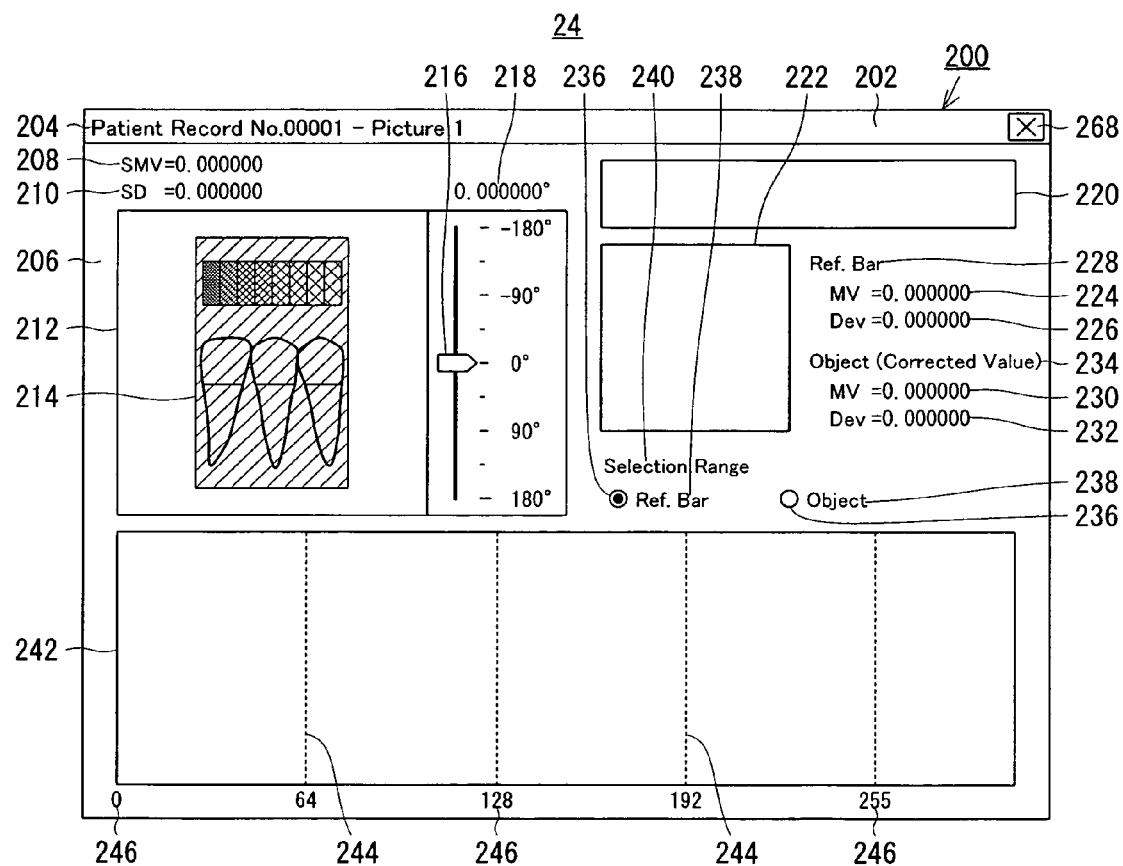
FIG. 9 is an illustration of an example of a subsidiary picture displayed on the PC display of the bone mineral density evaluating system of FIG. 1.

After X-rays 140 are displayed in the picture boxes 116, the radio button 124 for "Picture 1" is turned on, and the mouse 22 is used to select the region of the X-ray picture 140 for "Picture 1" to be evaluated. This causes the subsidiary picture 200 like the one shown in FIG. 9 is displayed on the display 24. A command for the region selection is stored in an "Editing" menu in the menu bar 106.

In the uppermost portion of the subsidiary picture 200 shown in FIG. 9, a horizontally elongated title bar 202 is displayed, containing horizontally aligned letter groups 204 indicating, for example, the patient's record number and the currently activated "Picture A", or "Picture 1" in the illustrated example, beginning from the left end of the bar 202. Below the title bar 202 is a rectangular frame region 206.

In the upper left area of the frame region 206, two letter groups 208 and 210 indicating the later-described standard mean value SMb and standard deviation SDb, respectively, are displayed one above the other. A generally square region selecting area 212 is displayed below the vertically arranged letter groups 208 and 210. In the region selecting area 212, an enlarged version 214 of the X-ray picture 140 corresponding to the currently activated "Picture A" is displayed. A slider 216 for rotating the enlarged picture 214 in the region selecting area 212 is displayed on the right side of the region selecting area 212. By sliding the slider 216 upward, for example, with the mouse 22, the enlarged picture 214 rotates counterclockwise. Conversely, if the slider 216 slides downward, the enlarged picture 214 rotates clockwise. The rotation angle is indicated by a letter group 218 displayed above the slider 216.

A horizontally elongated reference bar display area 220 is displayed in an upper right portion of the frame region 206. A generally square evaluation object display area 222 is displayed at a leftward location below the reference bar display area 220, in which an object to be evaluated is indicated. These areas 220 and 222 will be described in detail later.

Two letter groups 224 and 226 indicating the mean value Mb and deviation Db, which will be described later, are displayed one above the other in a region rightward of the evaluation object display area 222. Above the stack of the letter groups 224 and 226 displayed is a letter group 228 of "Reference Bar (Ref. Bar)" for the letter groups 224 and 226. Further, letter groups 230 and 232 for the corrected mean value Mo' and the corrected deviation Do', which will be described later, are displayed one above the other below the stack of the letter groups 224 and 226. Between the stack of the letter groups 224 and 226 and the stack of the letter groups 230 and 232, a letter group 234, "Evaluation Object (Corrected Value) (Object (Corrected Value))", which is a label for the letter groups 230 and 232, is displayed.

Two radio buttons 236 are horizontally aligned beneath the evaluation object display area 222, and beside the respective radio buttons, letter groups 238 indicating the names of the buttons are displayed. Above the radio buttons 236, a letter group 240 showing the functions to be selected by pressing them, namely, "Selection Range", is displayed.

A histogram display area 242 is displayed below the frame region 206. The histogram display area 242 will be described in detail later. Along the horizontal axis of the histogram display area 242, vertical scale lines 244 are displayed at constant intervals, and letters 246 indicating the index values for the scale lines 244 are displayed beneath the respective lines.

In FIG. 9, let it be assumed that the radio button 236 for "Reference Bar (Ref. Bar)" is clicked on by means of the mouse 22, and that a portion 250 defined by a broken line 248 shown in FIG. 10, which portion corresponds to the reference bar 36, is selected by means of the mouse 22 on the X-ray picture 214 displayed in the region selecting area 212. Specifically, a drawing starting point S for drawing a rectangle for selecting the area defined by the broken line 248 is set by means of the mouse 22, and the drawing ending point E for the rectangle 248 is set by drag-and-drop of the mouse 22. In this case, it is important that, in the length direction of the reference bar 250 (36) (i.e. in the horizontal direction in FIG. 10), one side of the rectangle 248 should align with one edge of the reference bar 250, with the other opposing side of the rectangle 248 aligned with the other edge of the reference bar 250. In the width direction of the reference bar 250 (i.e. in the vertical direction in FIG. 10), it is only necessary that the sides (i.e. the upper and lower sides) of the rectangle 248 be inward of the corresponding edges of the reference bar 250.

Figure 11:
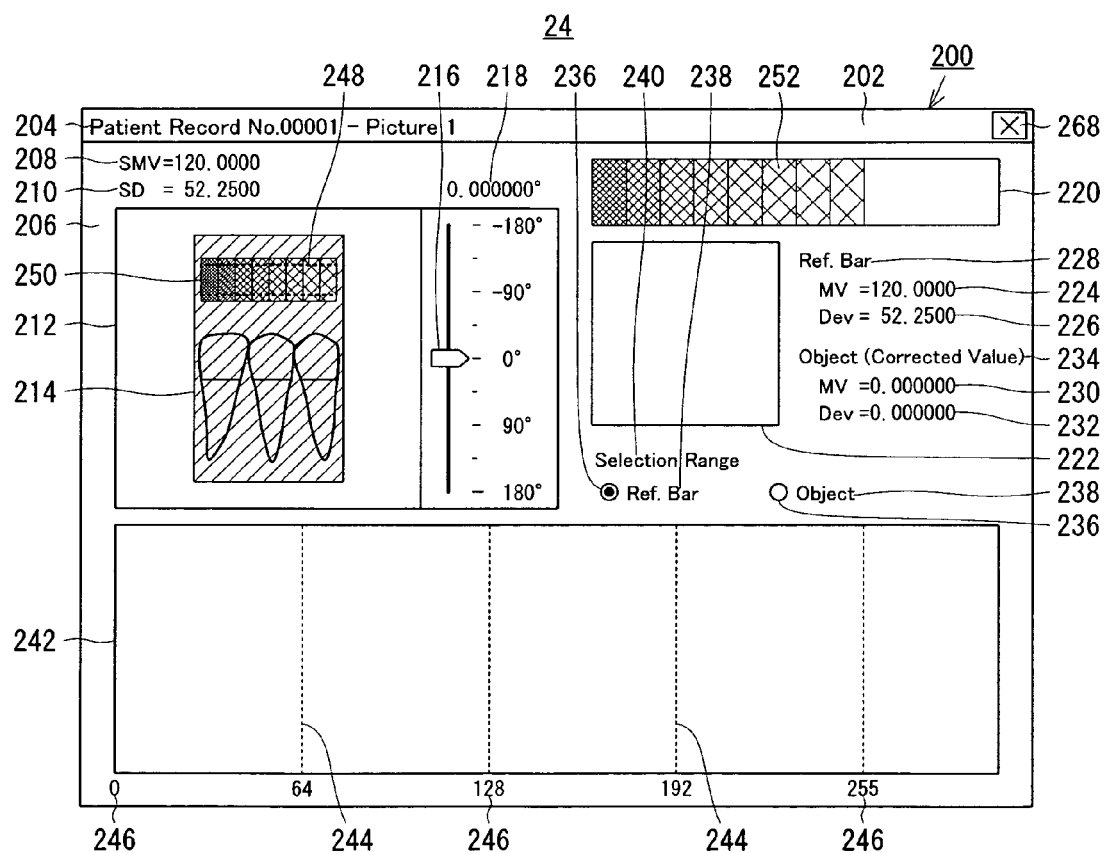
FIG. 11 is an illustration of an example of subsidiary picture different from the one shown in FIG. 9.
Figure 13:
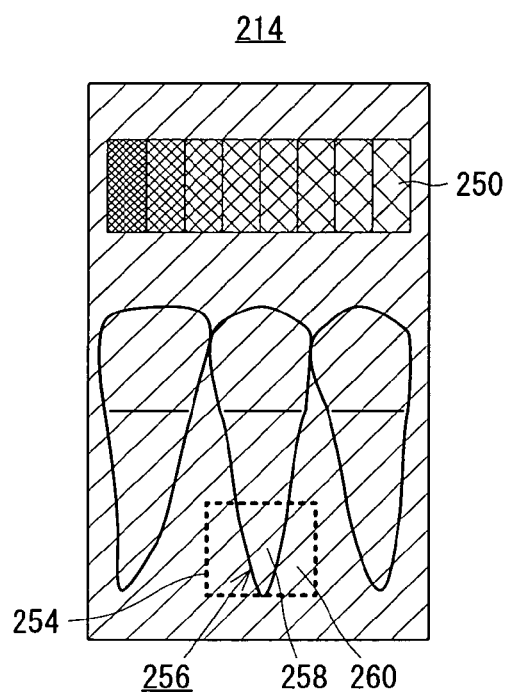
FIG. 13 is an enlarged illustration different from FIG. 10.

When the region 248 is selected as the reference bar 250 by means of the mouse 22, an enlarged picture 252 of the reference bar 250 is displayed in the reference bar display area 220, as shown in FIG. 11. Then, the brightness Yb[i,j] of each of pixels forming the reference bar region 248 is classified into one of 256 gradations, and the frequency Hb[x] of that gradation x is determined by the following Expression 1, where [i,j] is the coordinates of a particular pixel, and x is from 0 to 255.

$$Hb[x] = \frac{nb[x]}{Nb} \qquad \text{[Expression 1]}$$

In Expression 1, nb[x] is the number of pixels allotted to each gradation x, and Nb is the total number of pixels in the reference bar region 248. By dividing the number of pixels nb[x] for a given gradation x by the total number of pixels Nb, what is called a normalized frequency Hb[x] can be derived.

The result Hb of Expression 1 is recorded in a table 300 shown in FIG. 12, which is formed in the hard disc when the bone mineral density evaluation program is booted up.

Then, using the frequency Hb[x], the mean value Mb of the brightness Yb[i,j] and the deviation Db of the reference bar region 248 are calculated. The mean value Mb is determined by Expression 2, and the deviation Db is determined by Expression 3.

$$Mb = \sum_{x=0}^{255} \{x \cdot Hb[x]\} \quad \text{[Expression 2]}$$

$$Db = \sqrt{\sum_{x=0}^{255} \{(x - Mb)^2 \cdot Hb[x]\}} \quad \text{[Expression 3]}$$

The mean value Mb and the deviation Db calculated in accordance with Expressions 2 and 3 are also recorded in the table 300, and also displayed in the form of the letter groups 224 and 226 as shown in FIG. 11.

When the currently activated picture is "Picture 1", the mean value Mb and the deviation Db are set as the previously mentioned standard mean value SMb and the standard deviation SDb. In other words, the mean value Mb and the deviation Db recorded in the column for "Picture 1" in the table 100 of FIG. 12 are used as the standard mean value SMb and the standard deviation SDb. The standard SMb and the standard deviation SDb are displayed in the form of the letter groups 208 and 210 as shown in FIG. 11.

Let it be assumed that, after the reference bar region 248 is selected in the described manner, the radio button 236 for "Object to be Evaluated (Object)" is clicked on. Also, let it be assumed that a portion defined by a broken line 254 in FIG. 13 corresponding to the rectangular region 38 shown in FIG. 2 is selected on the X-ray picture 214 displayed in the region selecting area 212. That is, a portion 258 of a picture 256 of the first premolar 28 corresponding to the lower half of the tooth root 40, and a portion 260 corresponding to the alveolar bone 34 around the root 40 are enclosed by a rectangle 254 for region selection.

Figure 14:
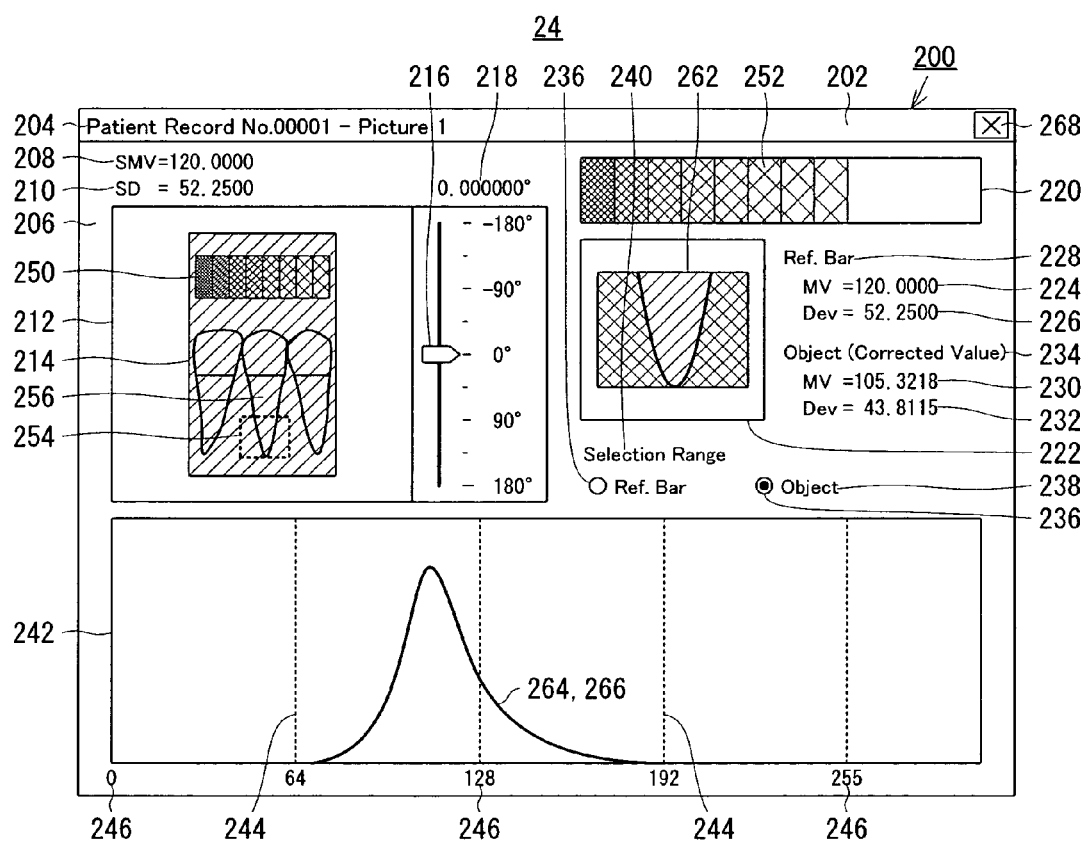
FIG. 14 is an illustration of an example of subsidiary picture different from FIG. 11.

Then, an enlarged version 262 of the region subject to evaluation within the rectangle 254 is displayed in the evaluation object display area 222, as shown in FIG. 14. The brightness Yo[i,j] of each of the pixels forming the region subject to evaluation (evaluation object region) 254 is classified into one of the 256 gradation steps, and the frequency Ho[x] is calculated for each gradation x based on the following Expression 4.

$$Ho[x] = \frac{no[x]}{No} \quad \text{[Expression 4]}$$

In Expression 4, no[x] is the number of pixels for the gradation x, and No is the total number of pixels of the evaluation object region 254. The result Ho of Expression 4 is recorded in the table 300 shown in FIG. 12.

The operation result Ho[x] of Expression 4 is used to calculate the mean value Mo and the deviation Do of the brightness Yo[i,j] in the evaluation object region 254. More specifically, the mean value Mo is determined in accordance with Expression 5, and the deviation Do is determined in accordance with Expression 6.

$$Mo = \sum_{x=0}^{255} \{x \cdot Ho[x]\} \quad \text{[Expression 5]}$$

$$Do = \sqrt{\sum_{x=0}^{255} \{(x - Mo)^2 \cdot Ho[x]\}} \quad \text{[Expression 6]}$$

The mean value Mo and the deviation Do calculated in accordance with Expressions 5 and 6 are also recorded in the table 300.

The previously discussed standard mean value SMb and the standard deviation SDb, and the mean value Mb and the deviation Db calculated in accordance with Expressions 2 and 3 are used to correct the brightness Yo[i,j] of the picture in the evaluation object region 254. That is, Expression 7 is used to determine the corrected brightness Yo'[i,j].

$$Yo'[i, j] = \frac{SDb}{Db} \cdot (Yo[i, j] - Mb) + SMb \quad \text{[Expression 7]}$$

In a similar manner to the one described with respect to Expressions 4 through 6, the frequency Ho'[x], the mean value Mo' and the deviation Do' for each gradation are determined based on the corrected brightness Yo'[i,j]. These corrected frequency Ho'[x], mean value Mo' and deviation Do' for each gradation are also recorded in the table 300. If the currently activated "Picture A" is "Picture 1", the corrected brightness Yo'[i,j] is equal to the uncorrected brightness Yo[i, j]. Accordingly, the corrected frequency Ho'[x] for each gradation, the corrected mean value Mo' and the corrected deviation do' are also equal to the uncorrected frequency Ho[x], mean value Mo and deviation Do. The corrected mean value Mo' and deviation Do' are displayed in the form of the letter groups 230 and 232 as shown in FIG. 14.

Two histograms according to the frequency Ho[x] for each gradation and the corrected frequency Ho'[x] for each gradation are displayed in the histogram display area 242. Specifically, two curves 264 and 266 for the frequencies Ho[x] and Ho'[x] are displayed, with the gradation x allocated along the abscissa and with the frequency along the ordinate. The two curves 264 and 266 are in different colors, for example, in blue and red, respectively. If the activated "Picture A" is "Picture 1", the curves 264 and 266 are displayed one on the other, for example, the curve 266 on the curve 263, so that it appears as if only one curve 266 were displayed. The scale lines 224 and the letter groups 246 indicating the values at the respective scale lines 224 are displayed for the respective gradations.

Figure 15:
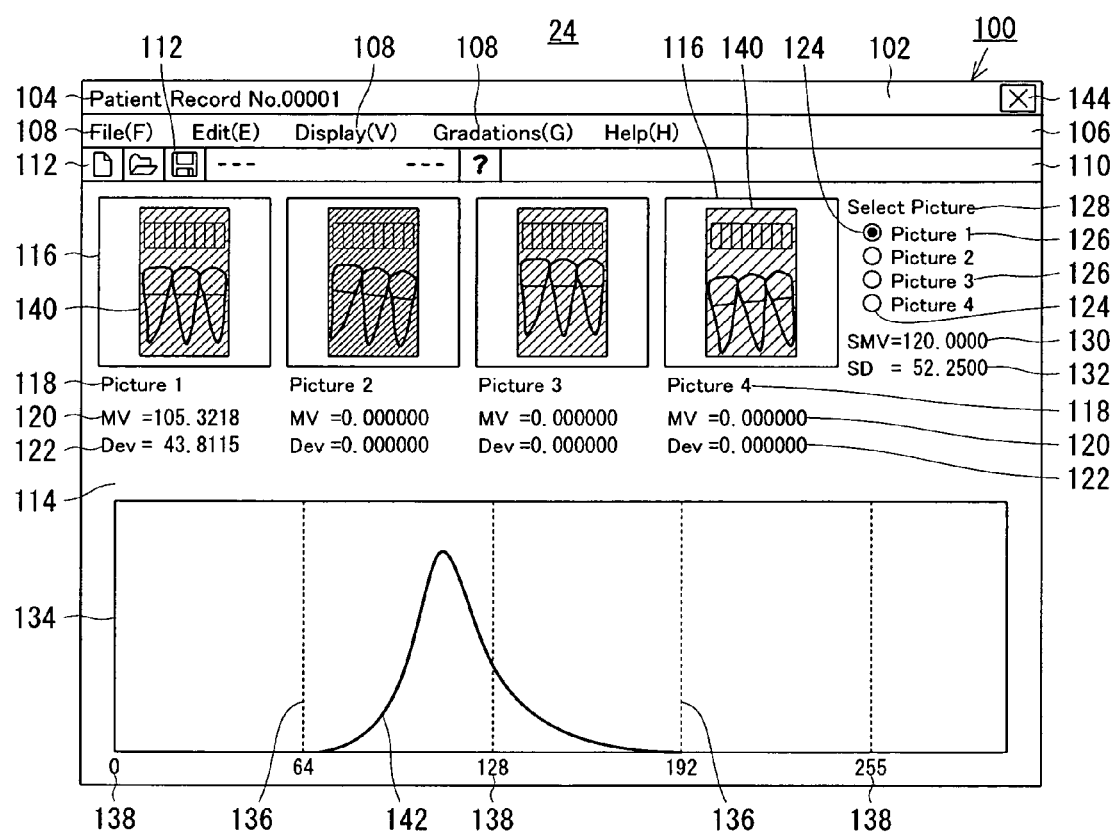
FIG. 15 is an illustration of a still another example of main picture different from the one of FIG. 8.

When a button "X" (closing button) 286 at the upper right end of the title bar 202 is clicked, with the subsidiary picture 200 like the one shown in FIG. 1 being displayed, the picture on the display 24 returns to the main picture 100 as shown in FIG. 15.

In the main picture 100 shown in FIG. 15, the corrected mean value Mo' and deviation Do' are displayed by the letter groups 120 and 122 beneath the picture box 116 for "Picture 1". The standard mean value SMb and deviation SDb are displayed by the letter groups 130 and 132 in the right portion of the main picture 100. A curve 142 similar to the curve 266 in FIG. 14, which is a histogram with the corrected frequency Ho'[x] allocated along the ordinate and with the gradation x allocated along the abscissa, is displayed in the histogram display area 134. In this histogram area 134, too, the scale lines 136 and the letter groups 138 showing the values at the respective scale lines are displayed at intervals of 64 gradations.

Figure 16:
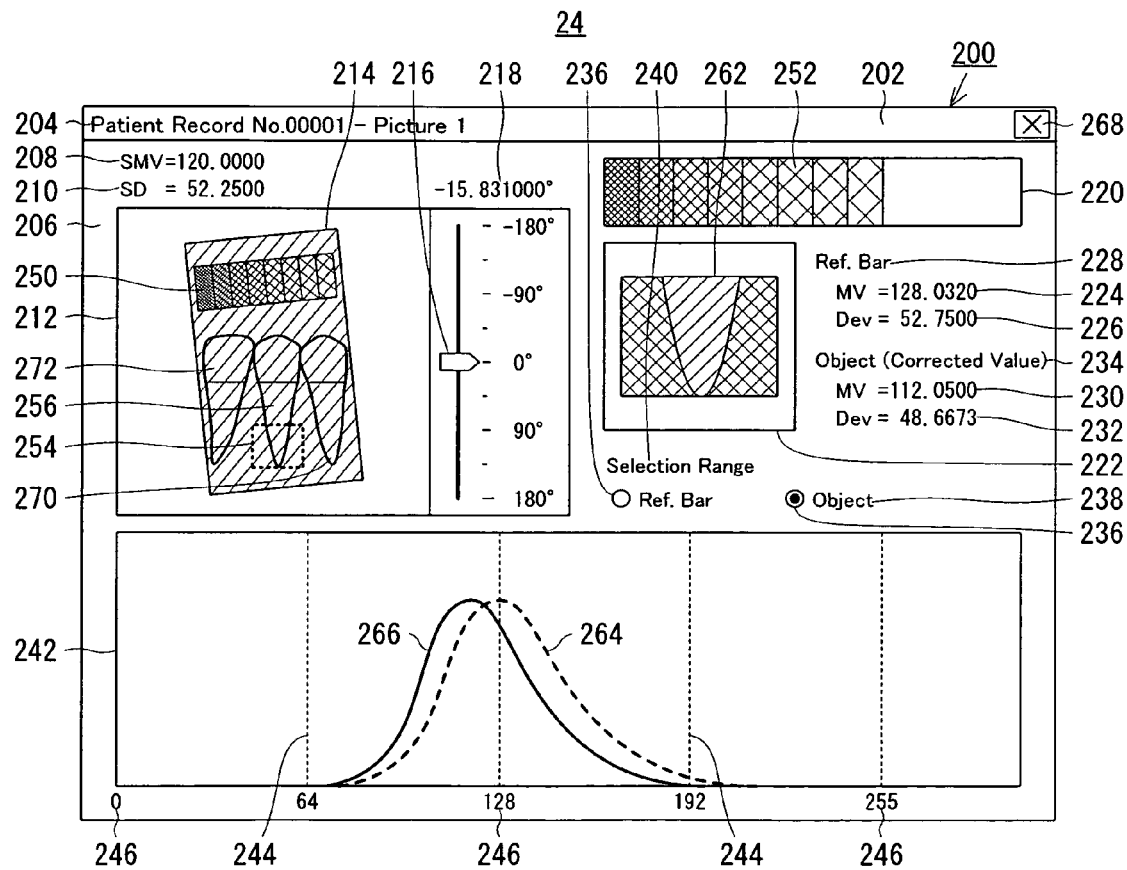
FIG. 16 is an illustration of a still another example of subsidiary picture different from the one shown in FIG. 14.

In the same manner, the subsidiary picture 200 is displayed for "Picture 2", and, on selecting the reference bar region 248 and the evaluation object region 254 on the subsidiary picture 200, the subsidiary picture 200 shown in FIG. 16 results.

The letter groups 224 and 226 displayed on the right side of the subsidiary picture 200 indicate the mean value Mb and deviation Db of the brightness Yb[i,j] of the reference bar region 248. In other words, the results of the arithmetic operation of Expressions 2 and 3, namely, Mb and Db, are displayed. The letter group 230 and 232 indicate the mean value Mo' and deviation Do' of the corrected brightness Yo'[i,j] of the evaluation object region 254. In other words, the results Mo' and Do' of the arithmetic operation on Expressions 5 and 6 are displayed. In addition, in the histogram display area 242, two curves 264 and 266 for the uncorrected frequency Ho[x] for each gradation and the corrected frequency Ho'[x] for each gradation are displayed in different colors. (In FIG. 16, the difference in color is represented by the use of different types of line.)

The meaning of the correction referred to herein, i.e. the correction according to Expression 7, is as follows. The correction made according to Expression 7 is to correct the brightness Yo[i,j] of the evaluation object region 254 of "Picture A" in such a manner that the brightness Yb[i,j] of the reference bar region 248 (FIG. 10) of "Picture A" can be equal to that of "Picture 1". In other words, the reference for the brightness Yo[i,j] of "Picture A" is made to mach the reference for the brightness Yo[i,j] of "Picture 1".

If the X-ray picture 214 displayed in the region selecting area 212 is tilted, as shown in FIG. 16, the tilt angle of the X-ray picture 214 is corrected by means of the slider 216. For example, if the reference bar 250 on the X-ray picture 214 is not horizontal, the tilt of the X-ray picture 214 is corrected so that the reference bar 250 becomes horizontal. The selection of the reference bar region 248 is made after the correction. In other case, the line along which the images 256, 270 and 272 of the teeth 28, 30 and 32 are lying may not be horizontal. In such a case, the tilt of the X-ray picture 214 is corrected in such a manner that the line becomes horizontal. The evaluation object region 254 is selected after that.

After the reference bar region 248 and the evaluation object region 256 are selected for "Picture 2", the reference bar region 248 and the evaluation object region 256 are selected for each of "Picture 3" and "Picture 4" in the same manner. After that, the display on the display screen 24 is returned to the main picture 100, which results in the main picture 100 shown in FIG. 17.

Figure 17:
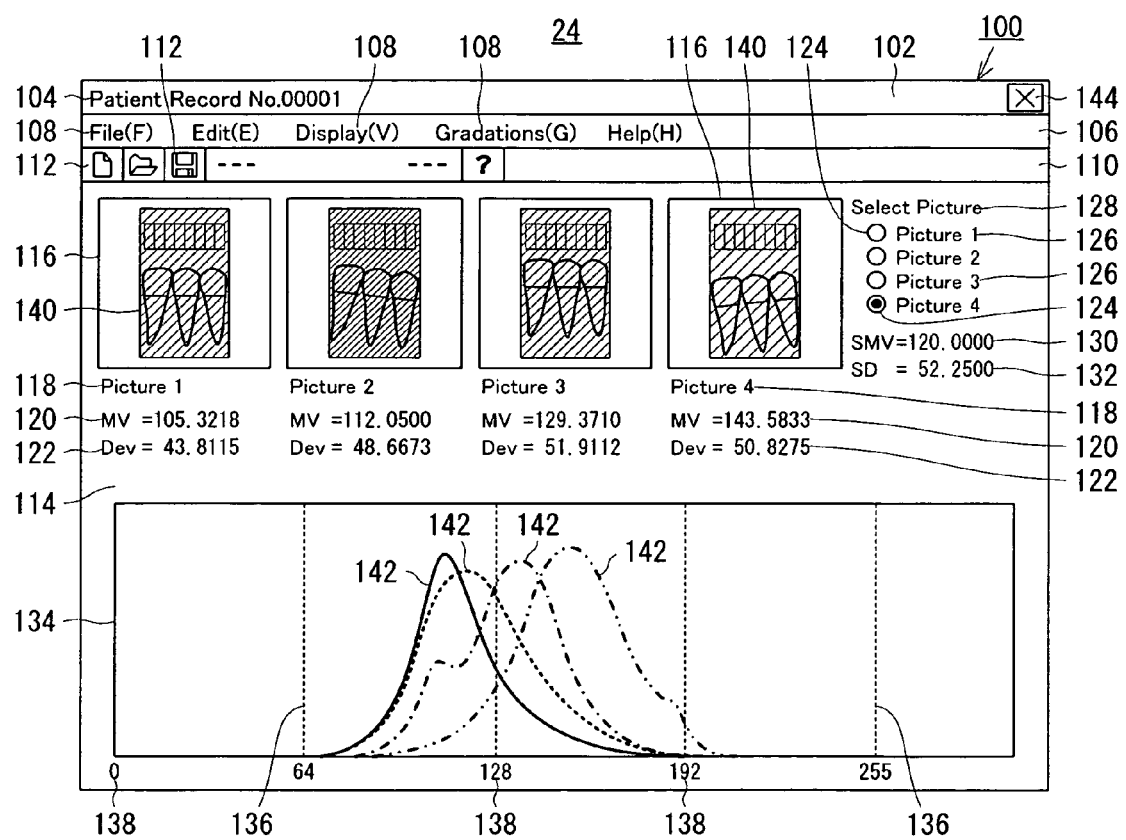
FIG. 17 is an illustration of a still further example of main picture different from the one shown in FIG. 15.

More specifically, in FIG. 17, the corrected mean value Mo' and deviation Do' of each "Picture A" are displayed by the letter groups 120 and 122 beneath each picture box 116, with the letter groups 130 and 132 in the right side portion of the main picture 100 indicating the standard mean value SMb and the standard deviation SDb. In the histogram display area 134, the histograms (curves 142, . . . ) according to the corrected frequencies Ho'[x] for each gradation of the respective "Pictures A" are displayed in different colors.

According to the first embodiment, as described above, the positions of the evaluation object regions 254 can be equally defined for each case, and the brightness Yo[i,j] of the evaluation object regions 254 can be corrected with respect to the fixed standard. Then, the corrected brightnesses Yo'[i,j] are used to compare the gradations or lightness and darkness of "Pictures A" taken on different days. In this manner, change in bone mineral density with time can be readily known from the comparison. Different from prior art visual evaluation of bone mineral density, the bone mineral density can be quantitatively or precisely evaluated.

The contents of the main picture 100 or the result of evaluation of bone mineral density shown in FIG. 17 can be recorded (stored) in the hard disc as described previously. The evaluation result can be printed on the patient record 42 by means of the laser printer 16. The command for recording or printing the evaluation results is stored in the "file" menu in the menu bar 106 in the main picture 100. By clicking an "X" button 144 on the right end of the title bar 102 of the main picture 100, the bone mineral density evaluation program is ended.

When the bone mineral density evaluation program is booted up as described above, the PC 12, or, more specifically, the CPU of the PC 12 executes the processing illustrated by flow charts shown in FIGS. 18-21.

Figure 18:
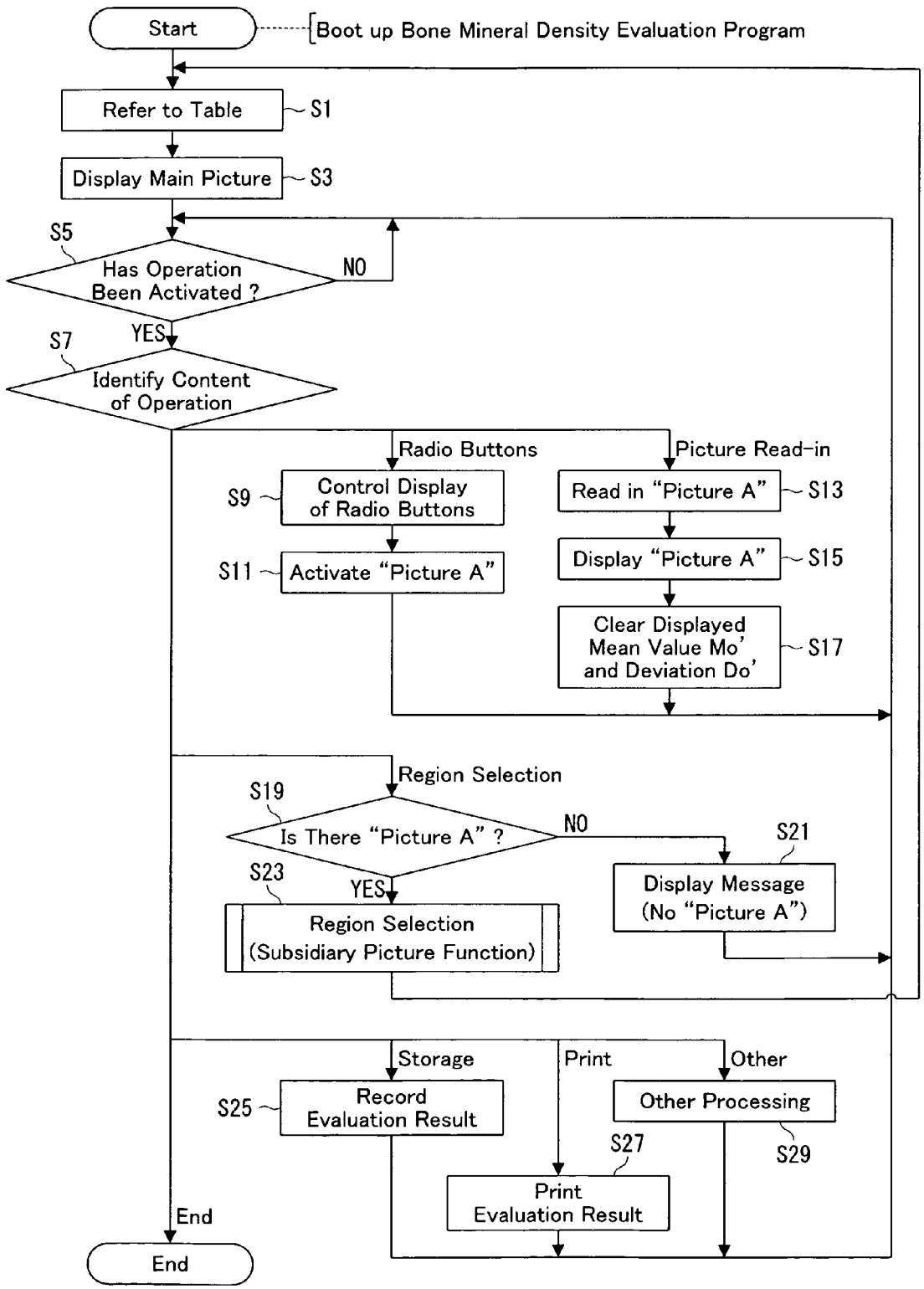
FIG. 18 is a flow chart of operation of the PC of the bone mineral density evaluating system of FIG. 1.

As shown in FIG. 18, when the bone mineral density evaluation program is booted up, the PC 12 advances to Step S1 for seeing the contents of the table 300 exemplified in FIG. 12. Then, it advances to Step S3 and displays the main picture 100 on the display 24 based on the results of Step S1.

After displaying the main picture 100, the PC 12 advances to Step S5 where it waits for some operation to be activated, or waits for a command. When some operation is activated, the PC 12 advances to Step S7 for identifying the contents of the operation.

If an operation to end the bone mineral density evaluation program is effected by clicking the X button 144 described above through the mouse 22, the PC 12 terminates the bone mineral density evaluation program.

If, on the other hand, any one of the radio buttons 124 is clicked (i.e. turned on), the PC 12 advances to Step S9 where it controls the manner of display of the respective radio buttons 124 such that only the clicked one of the radio buttons 124 is checked (i.e. a black point is added to the clicked button). The PC 12 advances to Steps S11 to activate the "Picture "A" ("A" being one of numerals 1-4) in accordance with the clicked radio button 124, and returns to Step S5.

If the PC 12 judges in Step S7 that a command to read in a picture from the hard disc has been given, it advances to Step S13. The picture is read in Step S13, and the PC 12 causes the read-in picture to be displayed in one of the picture boxes 116 corresponding to the "Picture A" in Step S15. In Step S17, the letter groups 120 and 122 for the corrected mean value Mo' and deviation Do' of "Picture A" are clicked to clear them (i.e. to make the numbers displayed become zeros). Then, the PC 12 returns to Step S5.

If the region selection is commanded in Step S7, the PC 12 advances to Step S19 and judges whether "Picture A" has been already read in or not. If "Picture A" has not yet been read in, the PC 12 advances to Step S21 to cause a message (not shown) stating that "Picture A" has not yet been read in to be displayed on the display 24. After displaying the message for a predetermined time, the PC 12 returns to Step S5.

If "Picture A" has already been read in, the PC 12 advances to Step S23 from Step S19 to execute the region selection, for achieving the functions displayed in the subsidiary picture 200. The detail of the region selecting processing will be given later. After the region selecting processing in Step S23, the PC 12 returns to Step S1.

If, in Step S7, the PC 12 judges that operation to store an evaluation result is activated, it advances to Step S25, where it records the evaluation results, or the contents of the main picture 100, in the hard disc and returns to Step S5.

If it is judged, in Step S7, that printing the evaluation result is required, the PC 12 advances to Step S27 and causes the laser printer 16 to print the evaluation result. After the completion of the printing, the PC 12 returns to Step S5.

If it is judged, in Step S7, that any other function than discussed above is required, the PC 12 performs the required processing and, then, returns to Step S5.

Figure 19:
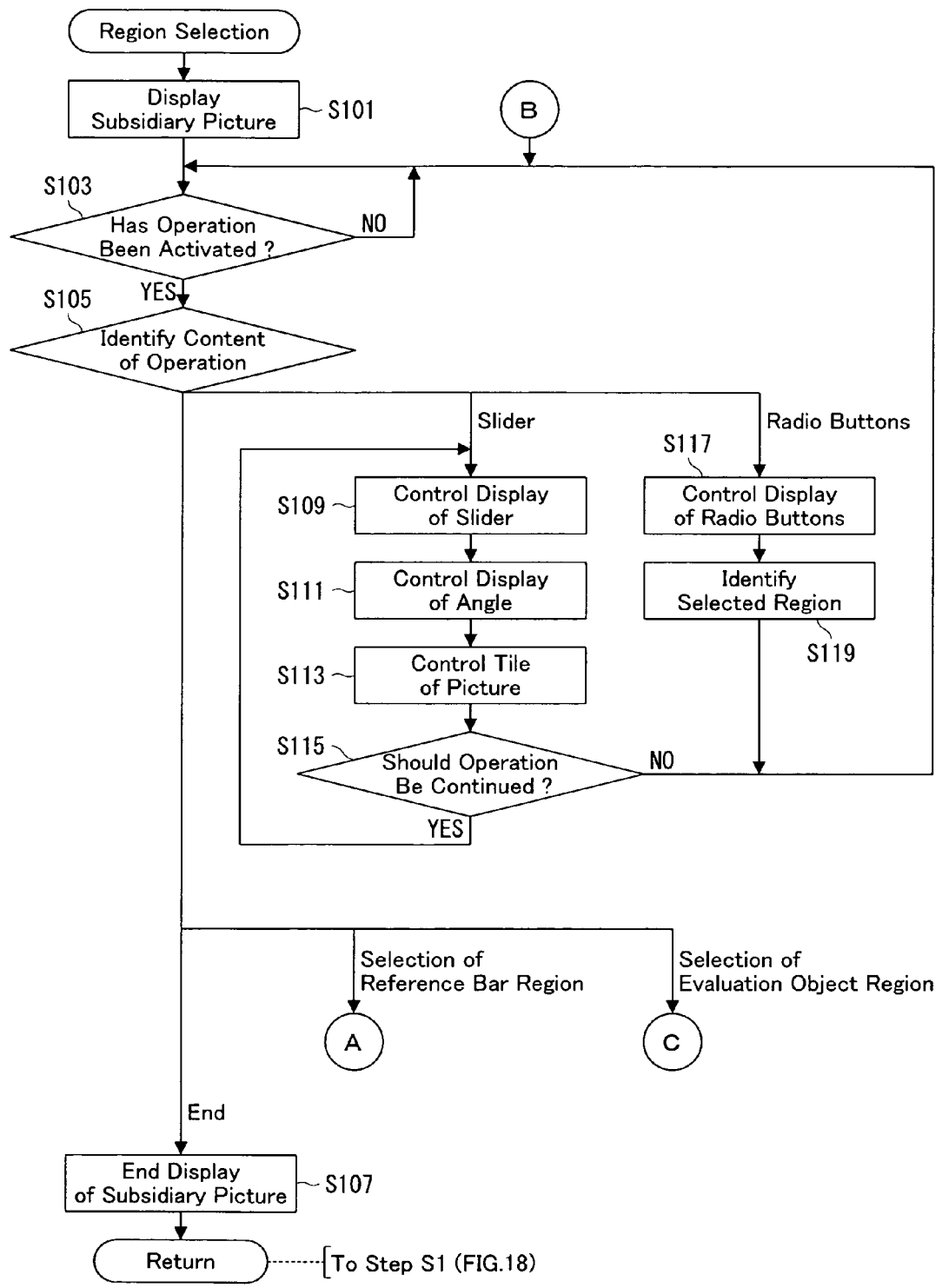
FIG. 19 is a flow chart of detail of a region selecting processing in the operation shown in FIG. 18.

In Step S23 for region selection, the PC 12 executes the following processing. As shown in FIG. 19, upon entering into the region selecting processing, the PC 12 first causes, in Step S101 shown in FIG. 19, the subsidiary picture 200 to be displayed on the display 24. Then, it waits for any operation to be activated and, when any operation is commanded, advances to Step S105 where it judges the content of the commanded operation.

If ending of the displaying of the subsidiary picture 200 is selected, i.e. if the X button 268 is clicked, the PC 12 advances to Step S107 where it causes the displaying of the subsidiary picture 200 to be ended, and returns to Step S1 in FIG. 18 to display the main picture 100 anew.

If the PC judges, in Step S105, that the slider 216 has been operated, it advances to Step S109, in which the displaying of the slider 216 on the subsidiary picture 200 is controlled in response to the operation of the mouse 22. The PC 12, in Step S111, controls the displaying of the letter group 218 (representing the rotation angle of the X-ray picture 214) in accordance with the position of the slider 216, and, in Step S113, controls the tilt of the X-ray picture 214. After that, the PC 12 advances to Step S115 where it judges whether or not the mouse 22 is still being operated. If the mouse 22 is still being operated, the PC 12 returns to Step S109, and, if the mouse 22 is not operated, the PC 12 returns to Step S103.

In Step S105, if the PC 12 judges that one of the radio buttons 236 has been clicked on, it advances to Step S117 to control the displaying of the radio buttons 236 so that only the clicked button 236 is checked. Then, the PC 12 sees, in Step S119, which region the clicked button 236 corresponds to, the reference bar region 248 or the evaluation object region 254. After that, the PC 12 returns to Step S103.

Figure 20:
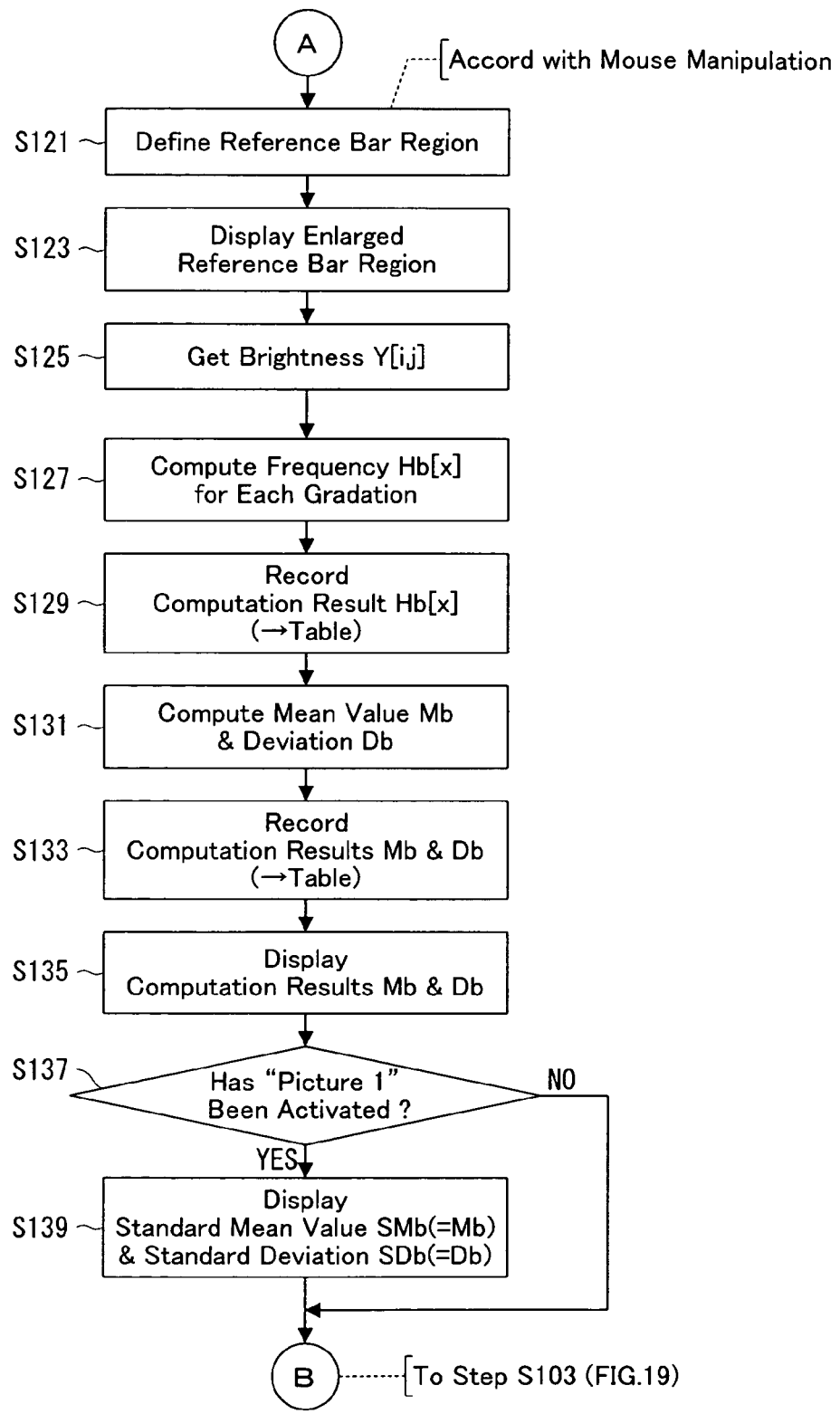
FIG. 20 is a flow chart following the one shown in FIG. 19.

If it is judged, in Step S105, that the mouse 22 has been operated within the region selecting area 212 on the X-ray picture 214, with the region 248 corresponding to the reference bar 36 being selected or, in other words, with the radio button 236 named "Reference Bar" being clicked on, the PC 12 advances to Step S121 shown in FIG. 20. In Step S121, the reference bar region 248 is defined in response to the operation of the mouse 22, and, after that, the PC 12 advances to Step S123 where the image of the reference bar region 248 is displayed, being enlarged, in the reference bar display area 220.

In Step S125, the PC 12 gets information of the picture brightness Yb[i,j] of the reference bar region, and classifies the brightness Yb[i,j] into 256 gradations. In Step S127, the PC 12 performs arithmetic operation for the frequency Hb[x] for each gradation in accordance with Expression 1 and records the results Hb[x] in the table 300 shown in FIG. 12 in Step S129.

In Step S131, the PC 12 calculates the mean value Mb in accordance with Expression 2, and the deviation Db in accordance with Expression 3, and records the results Mb and Db in the table 300 in Step S133. In Step S135, the PC 12 causes the mean value Mb and deviation Db to be displayed by means of the letter groups 224 and 226 and, after that, judges whether the currently activated picture is "Picture 1" or not in Step S137.

If "Picture 1" is judged to have been activated, the PC 12 advances to Step S139 where it causes the mean value Mb and deviation Db to be displayed as the standard mean value SMb and standard deviation SDb by means of the letter groups 208 and 210. After this step, the PC 12 returns to Step S103 in FIG. 19. On the other hand, if the currently activated picture is not "Picture 1", the PC 12 skips Step S139 and returns directly to Step S103.

Figure 21:
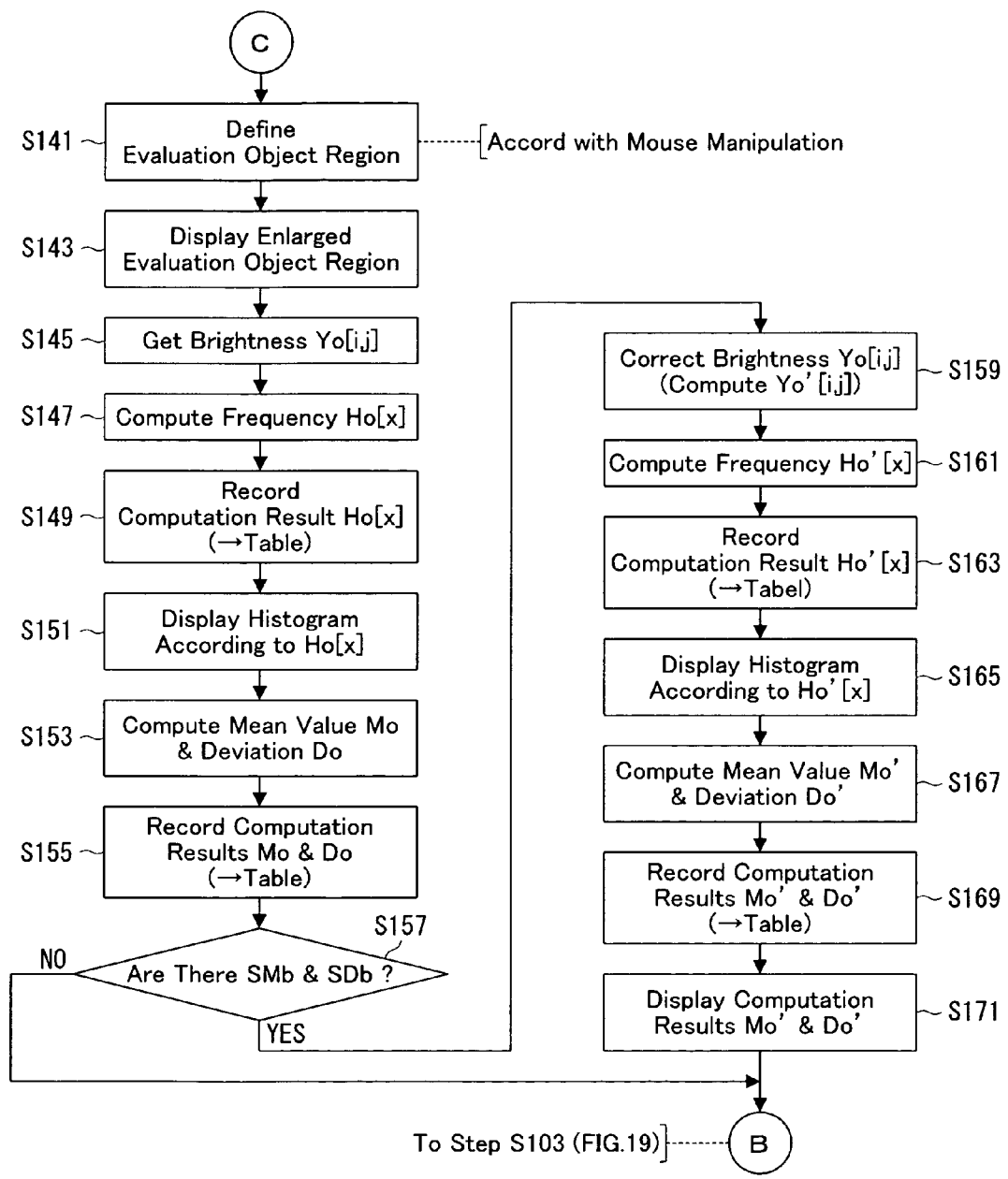
FIG. 21 is another flow chart following the one shown in FIG. 19.

If the PC 12 judges, in Step S105 of FIG. 19, that the mouse 22 has been operated on the X-ray picture 21 within the region selecting area 212 with the evaluation object region 254 selected or, in other words, the radio button 236 having a legend "Evaluation Object" clicked on, the PC 12 advances to Step S141 shown in FIG. 21. In Step S141, the evaluation object region 254 is set according to the operation of the mouse 22, and, thereafter, the PC 12 advances to Step S143 where it causes an enlarged version of the picture in the evaluation object region 254 to be displayed in the evaluation object display area 222.

Then, in Step S145, the brightness Yo[i,j] of the picture in the evaluation object region 254 is taken, and classified into 256 gradations. In Step S149, an arithmetic operation for the frequency Ho[x] for each gradation is performed according to Expression 4, and the results Ho[x] of the arithmetic operation is recorded in the table 300 shown in FIG. 12. Then, the PC 12, in Step S151, causes the histogram according to the frequencies Ho[x] for the respective gradations, or, in other words, the curve 264, to be displayed in the histogram display area 242.

After the execution of Step S151, the PC 12 advances to Step S153, where it calculates the mean value Mo, using Expression 5, and also the deviation Do, using Expression 6. The PC 12 records these results Mo and Do in the table 300 in Step S155. In Step S157, the PC judges whether the standard mean value SMb and the standard deviation SDb have been set or not.

If it is found that neither the standard mean value SMb nor the standard deviation SDb has been set yet, the PC 12 returns to Step S103 in FIG. 19. If they have been already set, the PC 12 advances to Step S159, where it calculates the corrected brightness Yo'[i,j], using Expression 7. The brightness Yo'[i,j] is also classified into 256 gradations.

The PC 12, then, advances to Step S161, where it calculates the frequencies Ho'[x] for the respective gradations based on the corrected brightness Yo'[i,j], and records the results Ho'[x] in the table 300 in Step S163. Then, in Step S165, the PC 12 causes the histogram or curve 266 according to the corrected frequencies Ho'[x] for the respective gradations to be displayed in the histogram display area 242.

The PC 12, in Step S167, calculates the mean value Mo' from the corrected frequencies Ho'[x] for the respective gradations, and also the deviation Do' from the corrected frequencies Ho'[x] for the respective gradations and the means value Mo'. In Step S169, the results Mo' and Do' are recorded in the table 300. The PC 12 causes the corrected mean value Mo' and deviation Do' to be displayed by the letter groups 230 and 232 in Step S171 and, after that, returns to Step S103 of FIG. 19.

As described, since the bone mineral density evaluation system according to the first embodiment of the present invention has a relatively simple and inexpensive arrangement as shown in FIG. 1, small-scale medical facilities, such as medical practitioners, can employ it economically easily. In addition, different from the previously described prior art, the bone mineral density can be evaluated quantitatively, and, therefore, it can be used to screen patients (i.e. to judge if the patients are suffering from osteoporosis) before providing dental treatment, which is significantly useful in planning the future dental treatment for a particular patient. For example, the system can be used in a pretest preceding implantation treatment which requires a patient to have a mandible strong enough for implantation.

In the first embodiment thus far described, the PC 12 is made to execute the bone mineral density evaluation program, and, therefore, the PC 12 functions as a bone mineral density evaluating apparatus, but the present invention is not limited to it. For example, a dedicated bone mineral density evaluating apparatus performing the same function as in the first embodiment can be used.

Also, in place of the film scanner 14 used as picture input means, photographic means, e.g. a CCD (Charge Coupled Device) camera, may be used. Alternatively, a digital cassette, which can directly take in a picture when a patient is being X-rayed. Also, in place of the laser printer 16, a printer employing other printing system, e.g. an ink-jet printer and a dot impact printer, may be used. Evaluation results may be recorded on a record medium, e.g. a magnetic card. Further, a picture to be inputted to and an evaluation result outputted from the PC 12 may be received and transmitted from and to a remote location through communications means like the Internet.

The specimen is not limited to the staircase-shaped aluminum block 36. Instead, an aluminum block having a uniform thickness may be used, or a block of a different material than aluminum may be used. In place of the aluminum block 36, a false bone having a known bone mineral density may be used. Based on the gradations of such false bone, the bone mineral density of a mandible and, hence a general or skeletal bone mineral density can be evaluated.

In the above-described example, four X-ray pictures 140, . . . , 140 are displayed together in the main picture 100, together with evaluation results (i.e. the corrected mean value Mo', the corrected deviation Do' and the histogram (the curve 142)) associated with each of the four X-ray pictures 140. In other words, the number of the X-ray pictures 140 is not limited to four, but any other number of the X-ray pictures and associated evaluation results may be displayed.

The brightness Yo[i,j] of a region 254 to be evaluated is corrected, using Expression 7, but an arithmetic expression (or algorithm) other than Expression 7 may be used.

The shape of the region 254 to be evaluated is not limited to a rectangle. For example, the portion 258 corresponding to the tooth root 40 (FIG. 2) may be excluded from the region 254 to be evaluated. The system may be arranged such that the shape of the region 254 can be set to any desired one, which can make the system flexibly and appropriately adapt itself to different shapes of mandibles (i.e. different alignments of a first premolar 28, a canine 30 and a second premolar 32) of various patients, which subtly differ from each other.

A portion other than the portion discussed with reference to the first embodiment (i.e. the lower half of the root 40 of the first premolar 28 and a portion around the alveolar 34) may be selected for the region 254 to be evaluated. Needless to say, similar portions must be selected for the region 254 for all the "Pictures A".

Next, a system according to a second embodiment of the invention is described with reference to FIGS. 22 through 40.

The brightness Yo[i,j] of the region 254 to be evaluated (see FIG. 13) is correlated with the bone mineral density, as described above. As the mean value Mo' of the corrected brightness Yo'[i,j] is larger, the bone mineral density is higher, and as the mean value Mo' is smaller, the bone mineral density is lower. The bone mineral density of thirty-five people (samples) of ages ranging from fifty to sixty-nine (averaging about sixty) were measured by known DXA (Dual Energy X-ray Absorptiometry), and the measurements (BMD (bone mineral density)) and the corrected mean values Mo' were compared. At the same time, T-values (the ratio of an actual BMD value of a person to the mean value of BMD values of people of ages ranging from twenty to forty-four) were compared with the corrected mean value Mo'. The results of comparisons are shown in FIG. 22.

As shown in FIG. 22, the corrected mean value Mo' tends to be larger for larger BMD values and smaller for smaller BMD values. This is supported by the fact that the coefficient of correlation between the BMD value and the corrected mean value Mo' is 0.6439, and it can be said that positive correlation exists between them. A similar analysis can be applied to the correlation with the T-values. Specifically, the coefficient of correlation between the T-values and the mean values Mo' is 0.6481, and there is positive correlation between them. From these facts, it is evident that a corrected mean value Mo' correlates to bone mineral density.

Generally speaking, bone mineral density is frequently evaluated on the basis of T-values. Specifically, if the T-value of a patient is 70% or less, the patient is diagnosed as having osteoporosis. A patient having a T-value of between 71% and 80% is diagnosed as having osteopenia. A T-value above 80% is diagnosed as being normal. A patient having a T-value above 100% is diagnosed as being extremely normal (healthy). The mean value of the corrected mean values Mo' in FIG. 22 for respective one of these ranges was calculated, which resulted in FIG. 23. This relation is represented by a graph in FIG. 24.

Figure 24:
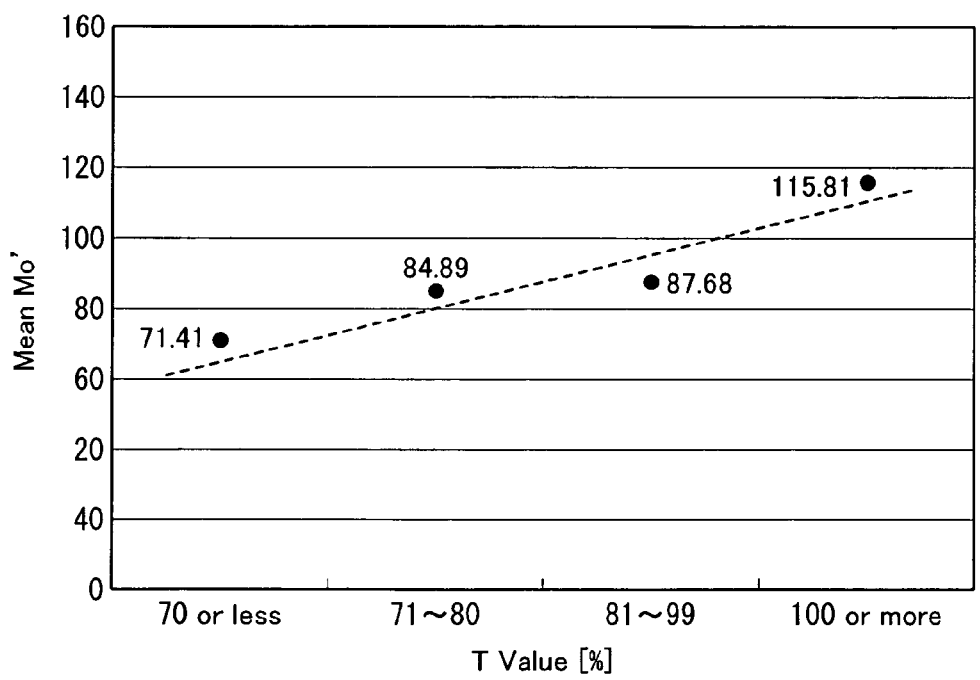
FIG. 24 is a graphical representation of the relationship shown in FIG. 23.

From FIGS. 23 and 24, too, it is seen that the corrected mean value Mo' correlates with the T-values and, hence, with the bone mineral density. Thus, it can be understood that a rough evaluation of a bone mineral density can be made based on the corrected mean value Mo'. For example, if the average of the corrected mean values Mo' is smaller than 71.41%, the patient is judged to have osteoporosis, or, strictly speaking, it is judged that the patient may have osteoporosis. If the average of the corrected mean values Mo' of a person is less than 84.89%, he or she has or may have osteopenia. Otherwise, the patient's bone mineral density can be judged to be normal.

According to the second embodiment, the function to judge the bone mineral density based on the corrected mean value Mo' is incorporated into the previously discussed bone mineral density evaluation program. In the above-described first embodiment, the brightness Y[i,j] of "Picture 1" is invariable, but, according to the second embodiment, the brightness Y[i,j] of "Picture 1" is corrected or modified according to a given basis. Otherwise, the second embodiment is same as the first one, and, therefore, those matters similar to matters of the first embodiment are not described in detail.

Figure 25:
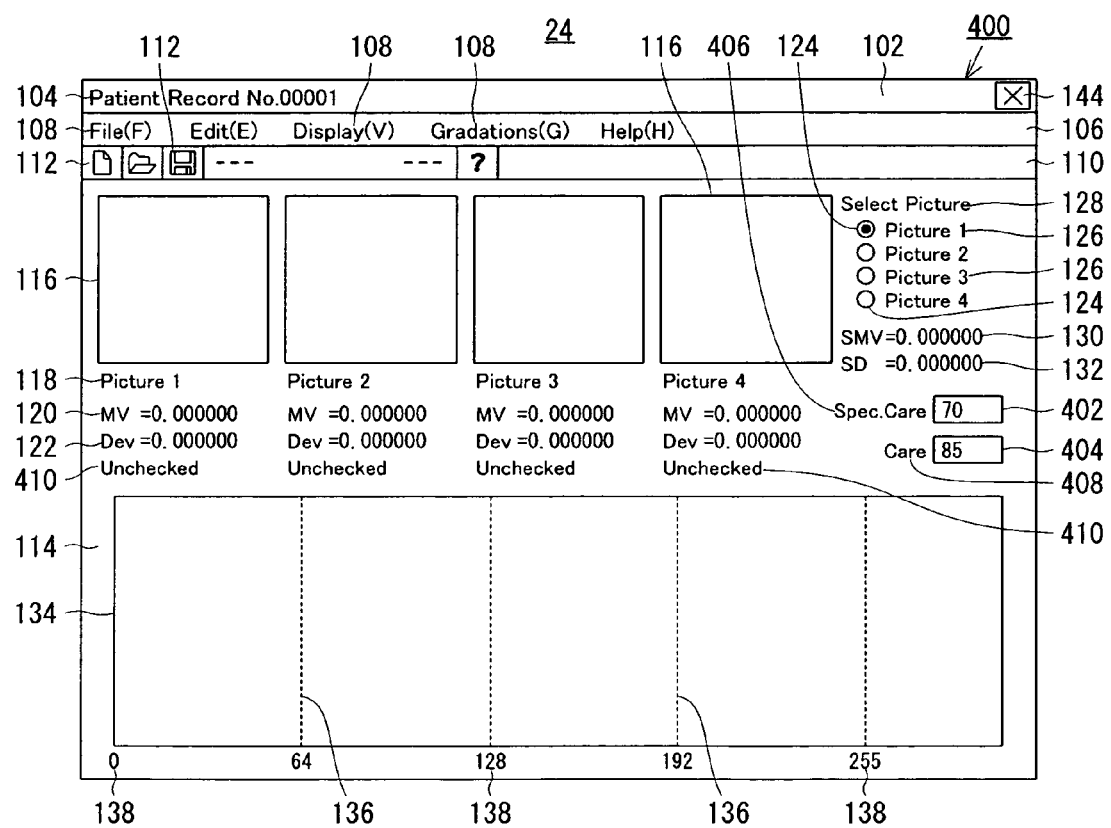
FIG. 25 is an illustration of a main picture displayed on a PC display of a bone mineral density evaluating system according to a second embodiment of the present invention.

Upon booting up of the bone mineral density evaluation program of the second embodiment, a main picture 400 as shown in FIG. 25 is displayed on the display screen 24 of the PC 12.

The main picture 400 is equivalent to the main picture 100 of the first embodiment (see FIG. 6 etc.) with edit boxes 402 and 404, letter groups 406 and 408, and letter groups 410 added thereto. The edit boxes 402 and 404 are displayed in the right middle portion of the frame region 114, being vertically aligned beneath the letter group 132 for the standard deviation SDb. The letter groups 406 and 408 are displayed respectively on the left sides of the edit boxes 402 and 404. The letter group 406 consists of letters expressing "Need Special Care (Spec. Care)", and the letter group 408 consists of letters expressing "Need Care (Care)". In one of the edit boxes, for example, the edit box 402 with the label (letter group) 406 of "Need Special Care" attached thereto, a value "70" which is an approximation of 71.41%, for example, is entered as a default value, which is a reference value for use in determining, based on the average of the corrected mean values Mo', whether a patient has osteoporosis. In the edit box 404 with the letter group 408, "Need Care" attached thereto, a value "85", an approximation of 84.89%, for example, is entered, which is used as a reference value for determining, based on the average of the corrected mean values Mo', whether a patient has osteopenia.

Beneath each picture box 116, three letter groups 118, 120 and 122 are displayed, and, beneath them, a letter group 410, representing a judgment made on the basis of the X-ray picture displayed in the associated picture box 116, is displayed. Although what are represented by the letter groups 410 (results of judgment) will be described in detail later, it is pointed out at present that the word "Unchecked" is displayed by the letter group 410 immediately after the booting up of the bone mineral density evaluation program.

Figure 26:
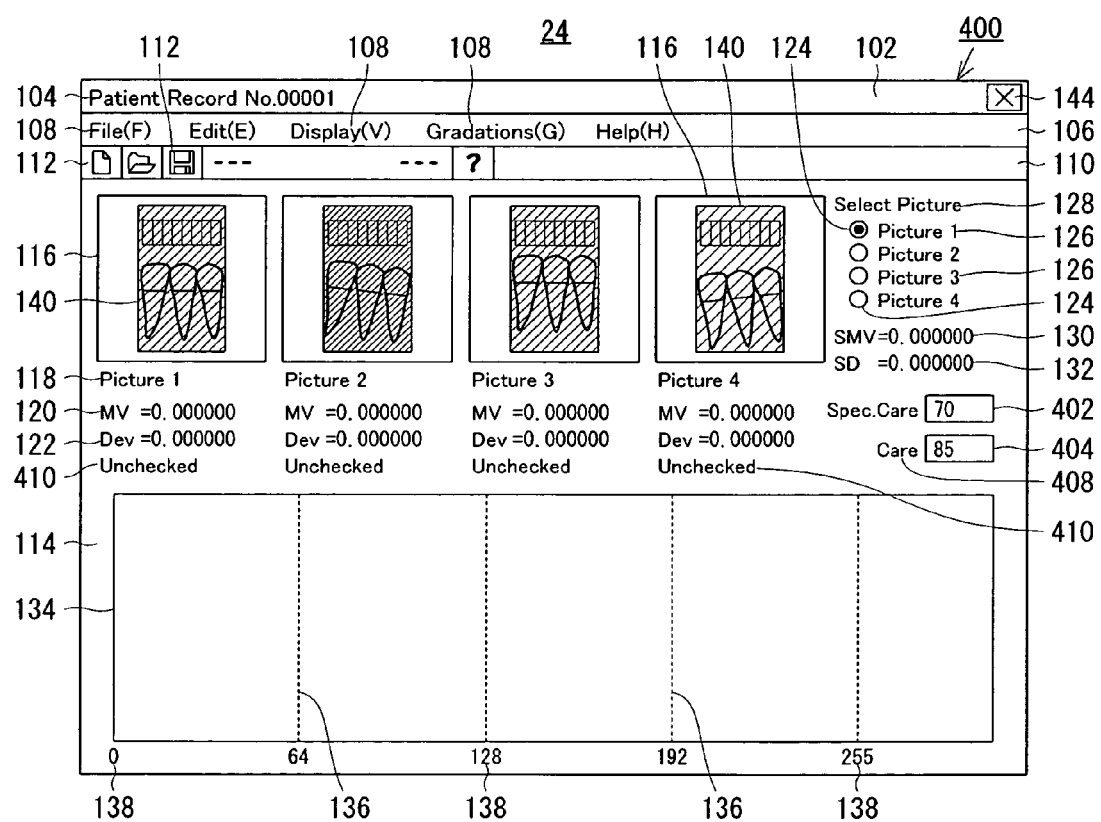
FIG. 26 is an illustration of a main picture different from the one shown in FIG. 25.
Figure 27:
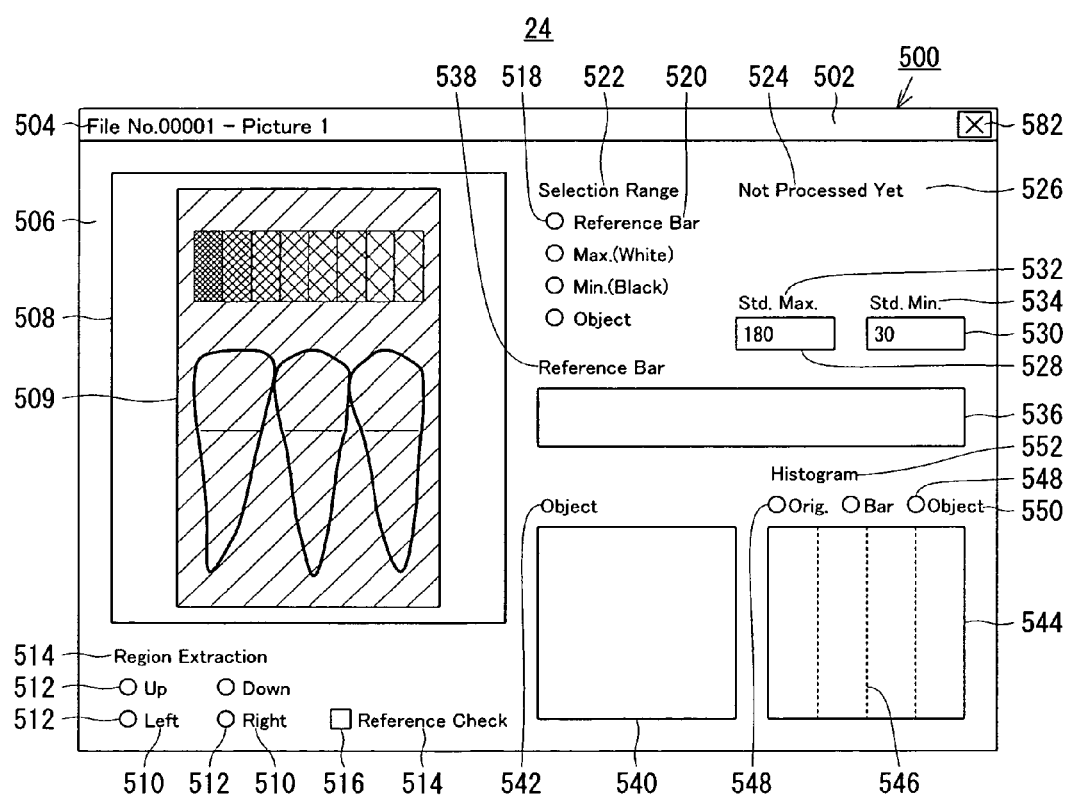
FIG. 27 is an illustration of a subsidiary picture derived from the main picture shown in FIG. 26.

Now, let it be assumed that, as in the first embodiment, picture data pieces corresponding to "Picture 1" through "Picture 4" are successively read in from the hard disc, causing the X-ray pictures 140 corresponding to "Picture 1" through "Picture 4" to be displayed in the picture boxes 116, as shown in FIG. 26, and that the operation to start the correction of brightness Y[i,j] is activated, with the radio button 124 for "Picture 1" turned on to enable "Picture 1". This causes a subsidiary picture 500 to be displayed on the display 24 as shown in FIG. 27. A command to commence the correction is stored in the "edit" menu in the menu bar 106.

As is seen in FIG. 27, in the uppermost portion of the subsidiary picture 500, a horizontally elongated title bar 502 is displayed as in the first embodiment. In this title bar 502, a group of horizontally aligned letters 504 is displayed starting at the left end, for example, which letter group indicates the patient's medical record number and the currently activated "Picture A" ("Picture 1" in the illustrated example). A rectangular frame region 506 is displayed beneath the title bar 502.

A region selecting area 508, which is larger than the region selecting area 212 in the subsidiary picture 200 of the first embodiment, is displayed in the left side portion of the frame region 206. An enlarged version 509 of the X-ray picture 140 of the currently activated "Picture A" is displayed in the region selecting area 508.

In the lower left corner of the frame region 506 below the region selecting area 508, four radio buttons 512 with respective letters 510 denoting "Up", "Below", "Left" and "Right" attached thereto are displayed, forming two rows and two columns. A letter group 514, denoting "Region Extraction", which is the function of the radio buttons 512, is displayed above the four radio buttons 512 (or letters 510). A check box 516 with a letter group 514 representing "Reference Check" is displayed on the right side of the radio buttons 512 (the letter groups 510).

In the upper portion of the frame region 506, on the right side of the region selecting area 508, four radio buttons 518 are arranged vertically, with letter groups 520 displayed rightward of the respective radio buttons 518. The respective letter groups 520 denote entries associated with the respective radio buttons 518, such as, for example, "Reference Bar", "Max. (White)", "Min. (Black)", and "Object to be Evaluated (Object)". Above the radio buttons 518 (the letter groups 520), displayed is a letter group 522 showing the function to be selected by pressing the buttons, namely, "Selection Range".

To the right of the group of the radio buttons 518, there is a note area 526 in which a note 524 can be displayed. Immediately after the subsidiary picture 500 is displayed, and before the later-mentioned correction processing is carried out on the subsidiary picture 500, a phrase "Not Processed Yet" is displayed as the note 524.

Two edit boxes 528 and 530 are horizontally arranged beneath the note area 526. Letter groups 532 and 534, "Standard Maximum (Std. Max.)" and "Standard Minimum (Std. Min.)", for the respective edit boxes 528 and 530 are displayed above the respective edit boxes 528 and 530. In one of the edit boxes 528 and 530, for example, in the edit box 528 with the entry (letter group) 532, "Standard Maximum" attached thereto, a later-described standard maximum value Ysmax is entered. In the state immediately following the displaying of the subsidiary picture 500, a default value of "180" is entered as the standard maximum value Ysmax. A standard minimum value Ysmin, which will be described later, is entered in the other edit box 530 with the labeling 534, "Standard Minimum" attached. In the state immediately following the displaying of the subsidiary picture 500, a default value of "30" is entered in the edit box 530.

Beneath the edit boxes 528 and 530, a horizontally elongated reference bar display area 536 is displayed. A letter group 538, "Reference Bar", for the reference bar display area 536 is displayed above the upper left corner of the reference bar display area 536.

A generally square evaluation object display area 540 is displayed beneath the left side portion of the reference bar display area 536. A letter group 542, "Evaluation Object (Object)", for the evaluation object display area 540 is displayed above the left side portion of the evaluation object display area 540.

Also, a generally square histogram display area 544 is disposed to the right of the evaluation object display area 540. Markings 546 are indicated at fixed intervals along the horizontal axis of the histogram display area 544. Three radio buttons 548 are horizontally arranged above the histogram display area 544. To the right of the respective radio buttons 548, letter groups 550, namely, "Original Picture (Orig.)", "Bar" and "Object", for the respective radio buttons 548 are displayed. A letter group 552 indicating the function of the radio buttons 548, namely, "Histogram", is displayed above the line of the radio buttons 548 (i.e. the letter groups 550).

Figure 10:
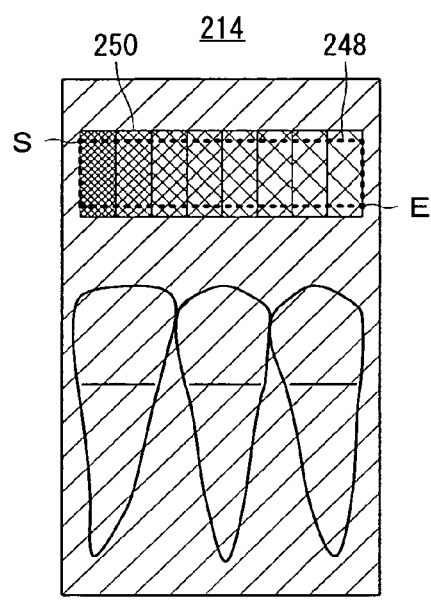
FIG. 10 is an enlarged illustration of a portion of the subsidiary picture shown in FIG. 9.
Figure 28:
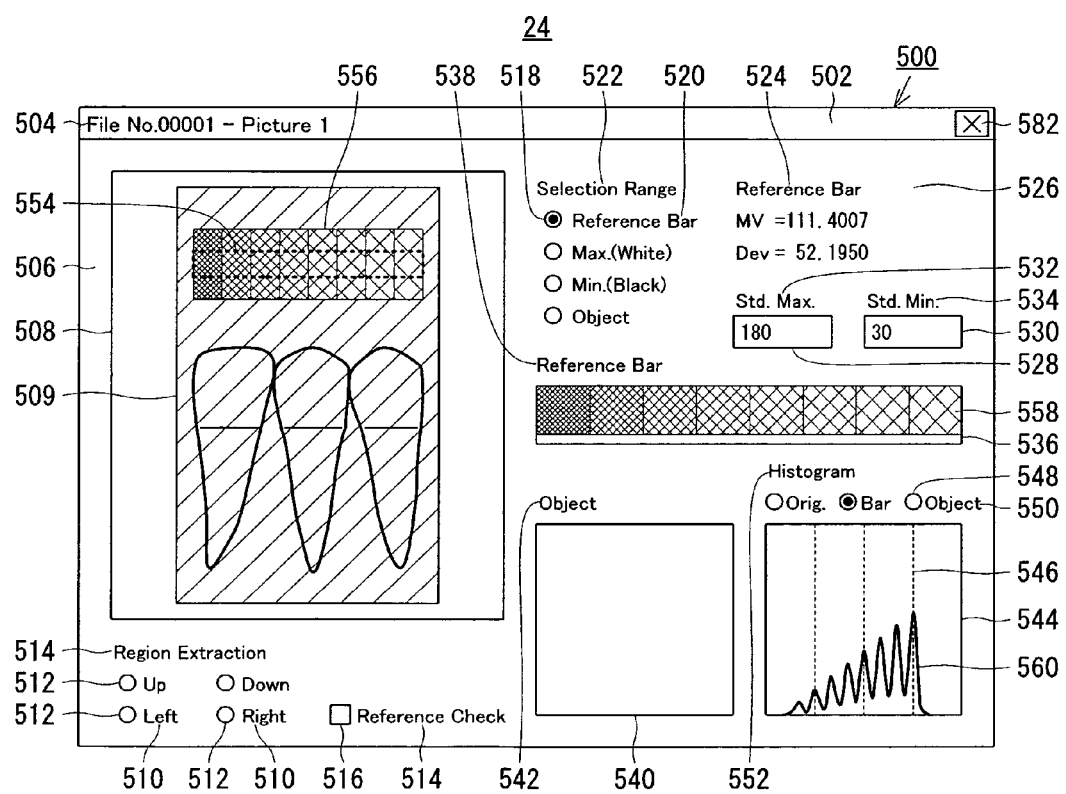
FIG. 28 is an illustration of a subsidiary picture different from the one shown in FIG. 27.

Let it be assumed that, while the above-described subsidiary picture 500 is being displayed, the radio button 518 with the label 520 of "Reference Bar", that is one of the four radio buttons 518 associated with the letter group 522, "Selection Range", is clicked ON as shown in FIG. 28. Further, let it be assumed that the mouse 22 (see FIG. 1) is used to select a portion 556 of an X-ray picture 509 displayed in the region selecting area 508, corresponding to the aforementioned reference bar 36 (see FIG. 2), as indicated by dotted lines 554. The selecting procedures are the same as those for selecting the portion 250 corresponding to the reference bar 36 in the first embodiment (FIG. 10).

After what may be called a reference bar region defined by the dotted lines 554 is selected, maximum and minimum values of the brightness Y[l,j] within the reference bar region 554 are determined. Basically, the maximum value is the brightness Y[l,j] of the portion of the reference bar region 554 corresponding to the portion onto which the aforementioned aluminum foil piece 48 is bonded (see FIG. 3). On the other hand, the minimum value is the brightness Y[l,j] detected at that portion of the reference bar region 554 which corresponds to the lowest step of the reference bar 36 (i.e. the portion having a thickness of Ta).

The determined maximum and minimum values are entered into a table 600 shown in FIG. 29, as a maximum brightness value Ybmax and a minimum brightness value Ybmin. The table 600 is formed in the hard disc when the bone mineral density evaluation program is booted up. The aforementioned standard maximum value Ysmax and standard minimum value Ysmin have been also recorded in the table 600.

The brightness Y[i,j] of the enlarged picture 509 displayed in the region selecting area 508 is corrected based on the maximum brightness value Ybmax, the minimum brightness value Ybmin, the standard maximum value Ysmax and the standard minimum value Ysmin, which have been recorded in the table 600. In other words, a corrected brightness Y'[i,j] is calculated in accordance with the following Expression 8.

$$Y'[i, j] = \Delta Y[i, j] + Y\text{smin} \quad \text{[Expression 8]}$$

where $$\Delta Y[i, j] = \frac{Y[i, j] - Yb\text{min}}{Yb\text{max} - Yb\text{min}} \cdot (Y\text{smax} - Y\text{smin})$$

Then, the enlarged picture 509 is re-displayed in the region selecting area 508 in accordance with the corrected brightness Y'[i,j] determined by Expression 8. In other words, the enlarged version 509 of the X-ray picture 140 prepared in accordance with the corrected brightness Y'[i,j] is displayed in the region selecting area 508.

The corrected brightnesses Y'[i,j] of all of the pixels of the X-ray picture 140 (or enlarged picture 509) are sorted into 256 gradations, and the frequency Hz'[x] for each gradation x is calculated in accordance with the following Expression 9, which is similar to Expression 1.

$$Ha'[x] = \frac{na'[x]}{Na} \quad \text{[Expression 9]}$$

In Expression 9, Na is the total number of pixels of the X-ray picture 140, and na'[x] is the number of pixels classified into a gradation x. The result Ha'[x] of the calculation according to Expression 9 is also recorded in the table 600.

Then, an enlarged version 558 of the reference bar region 554 having the corrected brightness Y'[i,j] is displayed in the reference bar display area 536. With respect to this reference bar region 554, too, the brightness Yb'[i,j] of each of the pixels forming the reference bar region 554 is classified into one of the 256 gradations, and a corrected frequency Hb'[x] for each gradation x is calculated in accordance with the following Expression 10.

$$Hb'[x] = \frac{nb'[x]}{Na} \quad \text{Expression 10}$$

In Expression 10, Nb is the total number of pixels constituting the reference bar region 554, and nb'[x] is the number of pixels classified into a gradation x. The results of the calculation according to Expression 10 are also recorded in the table 600.

Using the corrected frequency Hb'[x] calculated in accordance with Expression 10, the mean value Mb' of the corrected brightnesses Yb'[i,j] in the reference bar region 554 is calculated. Specifically, the corrected mean value Mb' is calculated in accordance with the following Expression 11, which is similar to Expression 2.

$$Mb' = \sum_{x=0}^{255} \{x \cdot Hb'[x]\} \quad \text{[Expression 11]}$$

The result Mb' of the calculation according to Expression 11 is also recorded in the table 600. If the currently activated picture is "Picture 1", the thus obtained corrected mean value Mb' is used as a later-mentioned standard mean value SMb.

Further, using the corrected frequency Hb'[x] and corrected mean value Mb', the deviation Db' of the corrected brightness Yb'[i,j] in the reference bar region 554 is calculated. Specifically, Expression 12, which is similar to Expression 3, is used to calculate the corrected deviation Db'.

$$Db' = \sqrt{\sum_{x=0}^{255} \{(x - Mb')^2 \cdot Hb'[x]\}} \quad \text{[Expression 12]}$$

The result Db' of the calculation according to Expression 11 is also recorded in the table 600. If the currently activated picture is "Picture 1", the thus obtained corrected deviation Db' is used as a later-mentioned standard deviation SDb.

The corrected mean value Mb' and corrected deviation Db' are displayed as the note 524 in the note area 526. Above the note area 526, a letter group "Reference Bar" is also displayed for the note 524.

Now, let it be assumed that one of the three radio buttons 548 associated with the letter group 552 for "Histogram", namely, the radio button with the label "Bar", is clicked on. This causes a curve (histogram) 560 according to the corrected frequency Hb'[x] of the reference bar region 552 to be displayed in the histogram display area 544. Thus, it is possible to know the distribution of the corrected brightness Yb'[x] of the reference bar region 552 from this curve 560.

Further, although not shown, when the radio button 548 with the label "Original Picture", is clicked on, a histogram based on the corrected frequency Hz'[x] of the entire X-ray picture 140 is displayed in the histogram display area 544. One can know, from such histogram based on the corrected frequency Ha'[x], the distribution of the corrected brightness Y'[i,j] of the entire X-ray picture 140. It should be noted that when the radio button 548 with the label 550, "Object", is clicked under this circumstance, nothing is displayed in the histogram display area 544.

Figure 30:
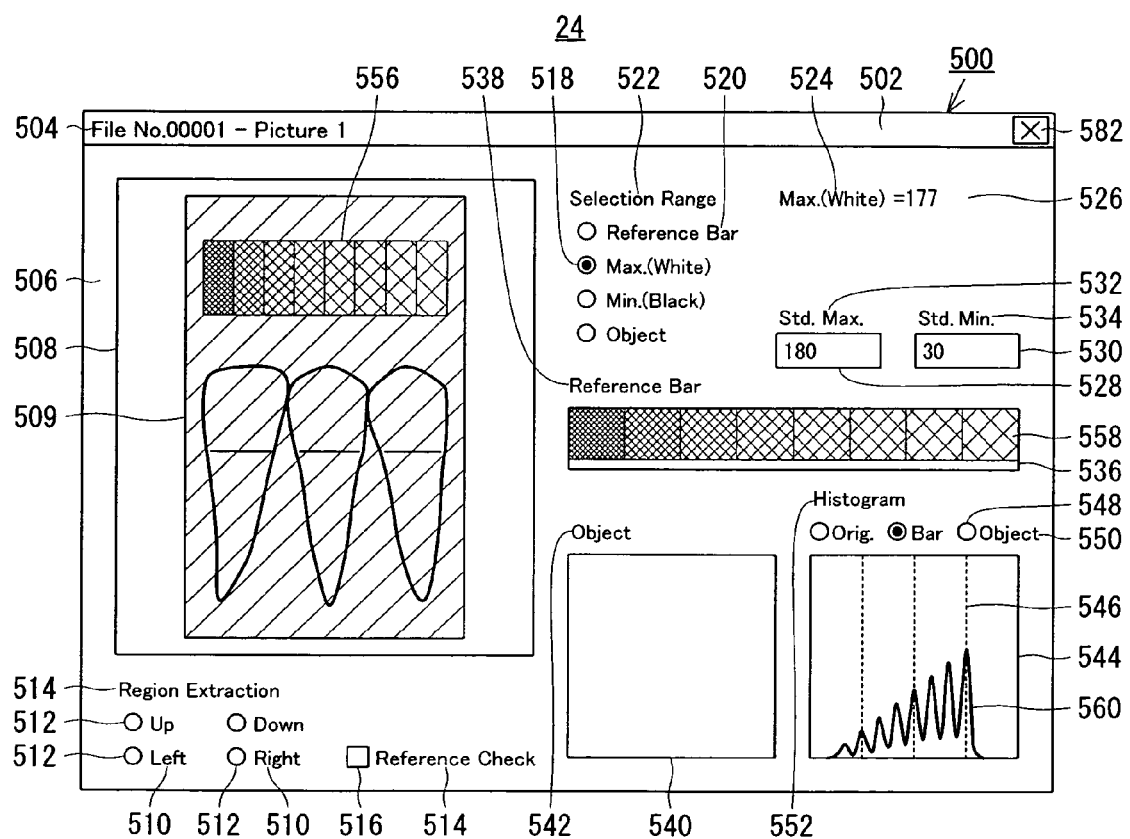
FIG. 30 is an illustration of a subsidiary picture different from the one shown in FIG. 28.

Next, let it be assumed that, as shown in FIG. 30, one of the four radio buttons 518 under the label 522 of "Selection Range", namely, the radio button 518 with the label 520 of "Maximum (White)" is turned on. By the turning on of the radio button 518 of "Maximum (White)", the radio button 518 for "Reference Bar" is turned off, and, at the same time, the reference bar region (dotted lines) 554 disappears.

When any point on the X-ray picture 509 within the region selecting area 508 in the state shown in FIG. 30 is clicked, the brightness Y[i,j] at the clicked point is set anew as the maximum brightness value Ybmax. In other words, the maximum brightness value Ybmax in the table 600 is renewed, and the renewed maximum brightness value Ybmax is displayed as the note 524 in the note area 526.

Then, the corrected brightness Y'[i,j] is corrected anew based on the renewed maximum brightness value Ybmax, and, based on the re-corrected brightness Y'[i,j], the frequency Ha'[x] for each gradation of the entire X-ray picture 114 (509), and the frequency Hb'[x] for each gradation, brightness mean value Mb' and brightness deviation Db' of the reference bar region 554 (enlarged picture 558) are re-corrected anew. The result of the correction is reflected onto the X-ray picture 509 displayed in the region selecting area 508, onto the enlarged picture 558 displayed in the reference bar display area 536, and onto the curve 560 displayed in the histogram display area 544.

The maximum brightness value Ybmax preferably is the brightness value Y'[i,j] at a location on the reference bar region 554 corresponding to the location at which the aluminum foil 48 is bonded, or, in other words, at the brightest (whitest) portion. Otherwise, a correct, corrected brightness Y'[i,j] might not be obtained. However, if the portion of the displayed X-ray picture 509 (114) corresponding to the aluminum foil 48 has not been properly X-rayed and if any one of the teeth 28, 30 and 32 has been treated with a metal, for example, if a gold or silver crown has been put on any one of the teeth 28, 30 and 32, the brightness Y'[i,j] at the portion corresponding to such metal is used as the maximum brightness value Ybmax, so that a relatively desirable corrected brightness Y'[i,j] can be provided even when the picture of the portion corresponding to the aluminum foil 48 is not satisfactory.

Figure 31:
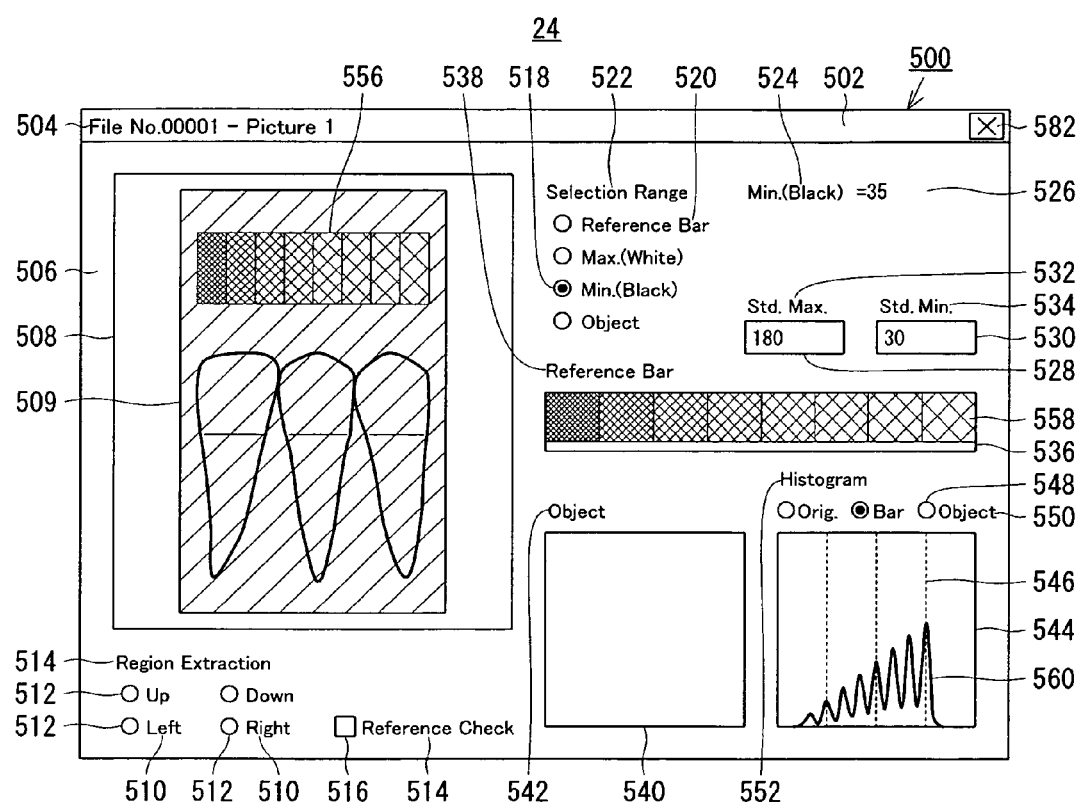
FIG. 31 is an illustration of a subsidiary picture different from the one shown in FIG. 30.

After that, as shown in FIG. 31, one of the four radio buttons 518 for the "Selection Range", which has a label 520, "Minimum Value (Black)" is assumed to be clicked ON. Then, when any location on the X-ray picture 509 is clicked, the brightness Y[i,j] at the clicked location is set anew as the minimum brightness value Ybmin. That is, the minimum brightness value Ybmin in the table 600 is renewed. The renewed minimum brightness value Ybmin is displayed as the note 524 in the note area 526.

Then, as in the case of the renewal of the maximum brightness value Ybmax, the corrected brightness Y'[i,j] is re-corrected based on the renewed minimum brightness value Ybmin. Then, based on the re-corrected brightness Y'[i,j], the frequencies Ha'[x] and Hb'[x] for each gradation, the mean brightness value Mb' and brightness deviation Db' are corrected anew, and the results of the correction are reflected onto the X-ray picture 509 in the region selecting area 508, onto the enlarged picture 558 in the reference bar display area 536, and onto the curve 560 in the histogram display area 544.

The minimum brightness value Ybmin is preferably the brightness Y[i,j] of the portion of the reference bar region 554 corresponding to the lowermost staircase step of the reference bar 36. However, if the lowermost staircase step portion of the reference bar 36 has not been X-rayed satisfactory, the brightness Y'[i,j] of the blackest (darkest) portion of the X-ray picture 509 is set, so that a relatively desirable corrected brightness Y'[i,j] can be obtained even when the picture of the lowermost step of the reference bar 36 is not satisfactory.

Figure 32:
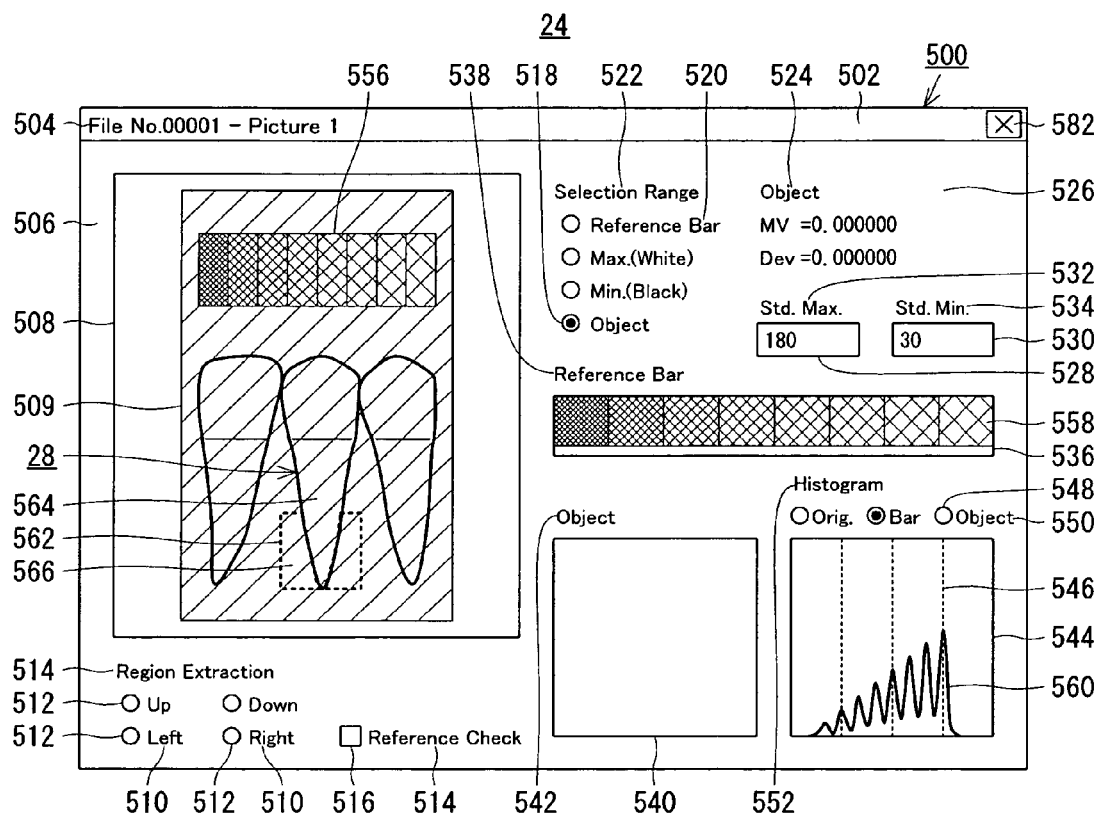
FIG. 32 is an illustration of a subsidiary picture different from the one shown in FIG. 31.
Figure 33:
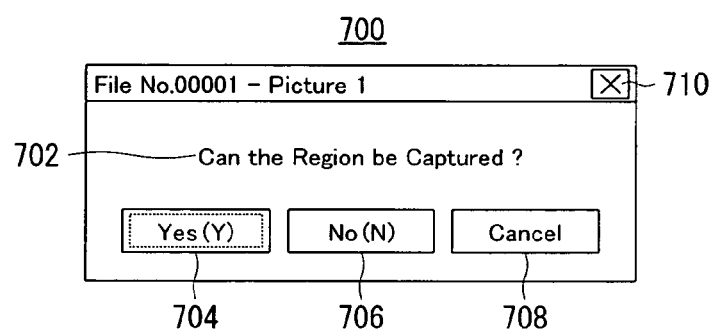
FIG. 33 is an illustration of a message box displayed following the display of the subsidiary picture of FIG. 32.

Thereafter, when one of the four radio buttons 518 with the labeling 520 of "Object to be Evaluated" is clicked on, as shown in FIG. 32, the selection of an evaluation object region 562 starts.

Specifically, as in the first embodiment (see FIG. 13), the mouse is operated on the X-ray picture 509 in the region selecting area 508 to select an evaluation object region 562. Although the shape of the evaluation object region 254 is limited to a rectangular shape in the first embodiment, the shape of the evaluation object region 562 of the second embodiment can be polygonal. Specifically, the start point to draw the evaluation object region 562 (framework) is determined by the first clicking of the mouse 22, and each of the successive clicking operations sets an apex of the area 562. Double clicking of the mouse 22 at the point same as the start point determines the end point of drawing the evaluation object region 562. Accordingly, it is possible to define, for example, a rectangular evaluation object region 562, but it is also possible to exclude a portion 564 corresponding to the tooth root 40 of the first premolar 28 from the evaluation object region 562, as shown in FIG. 32. In other words, it is possible to select only a portion 566 corresponding to the alveolar bone 34 around the tooth root 40, as the evaluation object region 562.

When the evaluation object region 562 is selected in the manner described above, a message box 700 shown in FIG. 33 is displayed over the subsidiary picture 500. In the message box 700, a letter group 702 is displayed, representing a question as to whether the selected evaluation object region 562 can be ultimate. For example, the letter group 702 can be: "Is It All Right to Capture the Region?" Below the letter group 702, three buttons 704, 706 and 708 with letter groups of "Yes", "No" and "Cancel", respectively, are displayed in a horizontal row.

By clicking the button 704 with the legend "Yes" in the message box 700, the evaluation object region 562 is finally decided. After that, the corrected frequency Ho'[x] of the finally decided evaluation object region 562 is determined in accordance with the following Expression 13 similar to Expression 4.

$$Ho'[x] = \frac{no'[x]}{No} \qquad \text{[Expression 13]}$$

In Expression 13, No represents the total number of pixels forming the evaluation object region 562, and no'[x] is the number of pixels for the gradation x. The results obtained in accordance with Expression 13 are recorded in the table 600.

Using the corrected frequency Ho'[x] determined in accordance with Expression 13, the mean value of the corrected brightness values Yo'[i,j] in the evaluation object region 562, i.e. the above-described corrected mean value Mo', is determined. Specifically, the corrected mean value Mo' is determined in accordance with the following Expression 14, which is similar to Expression 5.

$$Mo' = \sum_{x=0}^{255} \{x \cdot Ho'[x]\} \qquad \text{[Expression 14]}$$

The result of the computation according to Expression 14 is also recorded in the table 600, and, using the corrected mean value Mo' determined by Expression 14 and the corrected frequency Ho'[x], the corrected deviation Do' of the corrected brightness Yo'[i,j] in the evaluation object region 562 is determined. Specifically, the corrected deviation Do' is determined in accordance with the following Expression 15, which is similar to Expression 6. The results of the computation according to Expression 15 are also recorded in the table 600.

$$Do' = \sqrt{\sum_{x=0}^{255} \{(x - Mo')^2 \cdot Ho'[x]\}} \qquad \text{[Expression 15]}$$

Figure 34:
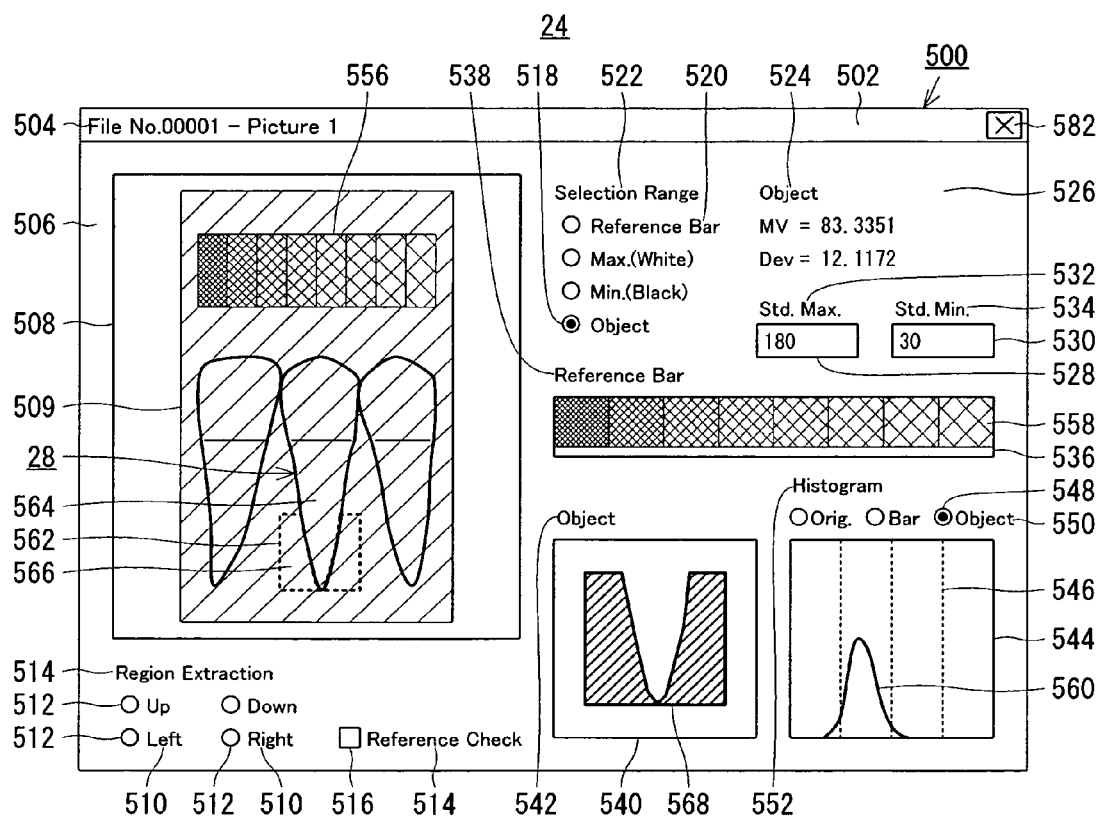
FIG. 34 is an illustration of a subsidiary picture different from the one shown in FIG. 32.

After the corrected frequency Ho'[x], corrected mean value Mo' and corrected deviation Do' are obtained for the evaluation object region 562 in the manner described above, the message box 700 disappears, and the subsidiary picture 500 changes to the one shown in FIG. 34.

Specifically, an enlarged version 568 of the evaluation object region 562 is displayed in the evaluation object display area 540, and letter groups showing the corrected mean value Mo' and corrected deviation Do' are displayed as the note 524 in the note area 526. A letter group for an entry "Object to Be Evaluated (Object)", is displayed also as the note 524, in the upper portion of the note area 526.

Now, let it be assumed that the rightmost one of the three radio buttons 548 associated with the above-mentioned "Histogram", with a label "Object" attached thereto, is clicked on. This causes a curve 560 according to the corrected frequency Ho'[x] of the evaluation object region 562 to be displayed in the histogram display area 544. From this curve 560, it is possible to know the distribution of the corrected brightness Yo'[i,j] in the evaluation object region 562.

Clicking on of the radio button 548 labeled "Original Picture" causes a histogram according to the corrected frequency Ha'[x] of the whole X-ray picture 140 to be displayed in the histogram display area 544, as described previously. If the radio button 548 labeled "Bar" is clicked, a histogram according to the corrected frequency Hb'[x] of the reference bar region 552 is displayed.

When the maximum brightness value Ybmax is renewed as described above after the evaluation object region 562 is determined, the corrected brightness Y'[i,j] is re-corrected based on the renewed maximum brightness value Ybmax, and, in association therewith, the corrected frequency Ho'[x], corrected mean value Mo' and corrected deviation Do' of the evaluation object region 562 are corrected anew. The results of the corrections are reflected onto the enlarged picture 568 in the evaluation object display area 540 and onto the curve 560 in the histogram display area 544. Similar operations take place when the minimum brightness value Ybmin is renewed.

Returning to FIG. 33, if the button 706 with the legend "No" is clicked, the message box 700 disappears, and the subsidiary picture 500 re-appears. On the subsidiary picture 500, the shape and size of the evaluation object region 562 can be altered as desired. The altering procedure is similar to a procedure employed by conventional image editing software, and, therefore, no detailed description is given here.

Clicking the button 708 with the legend of "Cancel" in the message box 700 causes the message box 700 to disappear and also causes the subsidiary picture 500 to return to the initial state before setting the start point of delineating the evaluation object region 562. The same occurs when a closing button 710 with a mark "X" in the upper right corner of the message box 700 is clicked.

In the subsidiary picture 500, if the value in the edit box 528 with the legend 532, "Standard Maximum Value", is changed, the standard maximum value Ysmax in the table 600 is renewed accordingly. Then, the corrected brightness Y'[i,j] is corrected anew according to the renewed standard maximum value Ysmax, which results in correcting anew of the respective parameters in the table 600, namely, the respective corrected frequencies Ha', Hb' and Ho', the corrected mean values Mb' and Mo', and the corrected deviations Db' and Do'. The results of the corrections are reflected onto the X-ray picture 509 in the region selecting area 508, the enlarged picture 568 in the evaluation object display area 540, and the curve 506 in the histogram display area 544. Similar events occur when the value in the edit box 530 with the legend 534, "Standard Minimum Value", is altered. It should be noted that, since the standard maximum value Ysmax and the standard minimum value Ysmin essentially are standard values, it is not desirable to alter them unnecessarily. Accordingly, it is desirable to alter these values only when the maximum or minimum brightness value Ybmx or Ybmin cannot be precisely derived due to, for example, unsatisfactory X-raying of the reference bar region 554.

As described above, according to the second embodiment, a polygonal shape can be selected as the shape of the evaluation object region 562, but it sometimes may be difficult to delineate a region having a fixed shape and size as the evaluation object region 562. To make it possible to set an evaluation object region 562 having a fixed shape and size in the system according to the second embodiment, a region setting support function is provided.

Figure 35:
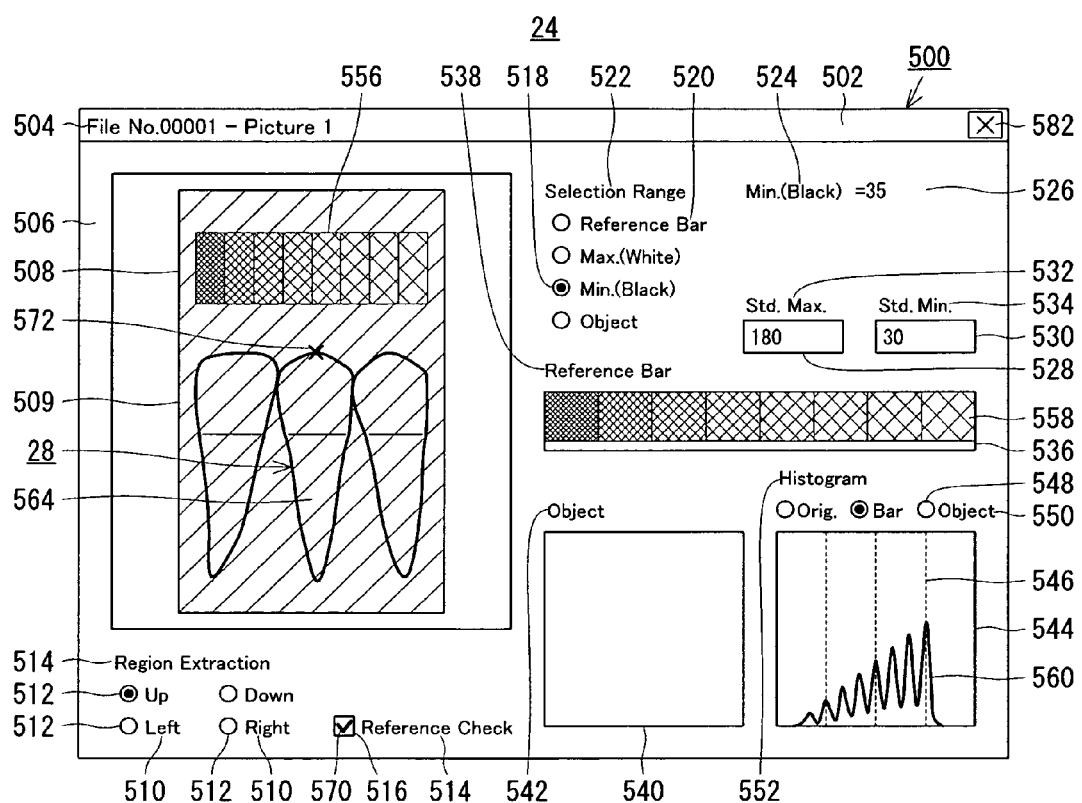
FIG. 35 is an illustration of a subsidiary picture different from the one shown in FIG. 34.

When the check box 516 with the legend 514, "Reference Check", is clicked, a check 570 is inputted in the check box 516 as shown in FIG. 35, enabling the region setting support function described above. Now, let it be assumed that one of the four radio buttons 512 below the letter group 514 of "Region Extraction", e.g. the radio button 512 with the letter group 510 of "Up", is clicked on. In this state, when a portion of the X-ray picture 509 corresponding to the topmost portion of the first premolar 28 is clicked, a predetermined mark 572, e.g. a mark "X", is attached to that portion.

Figure 36:
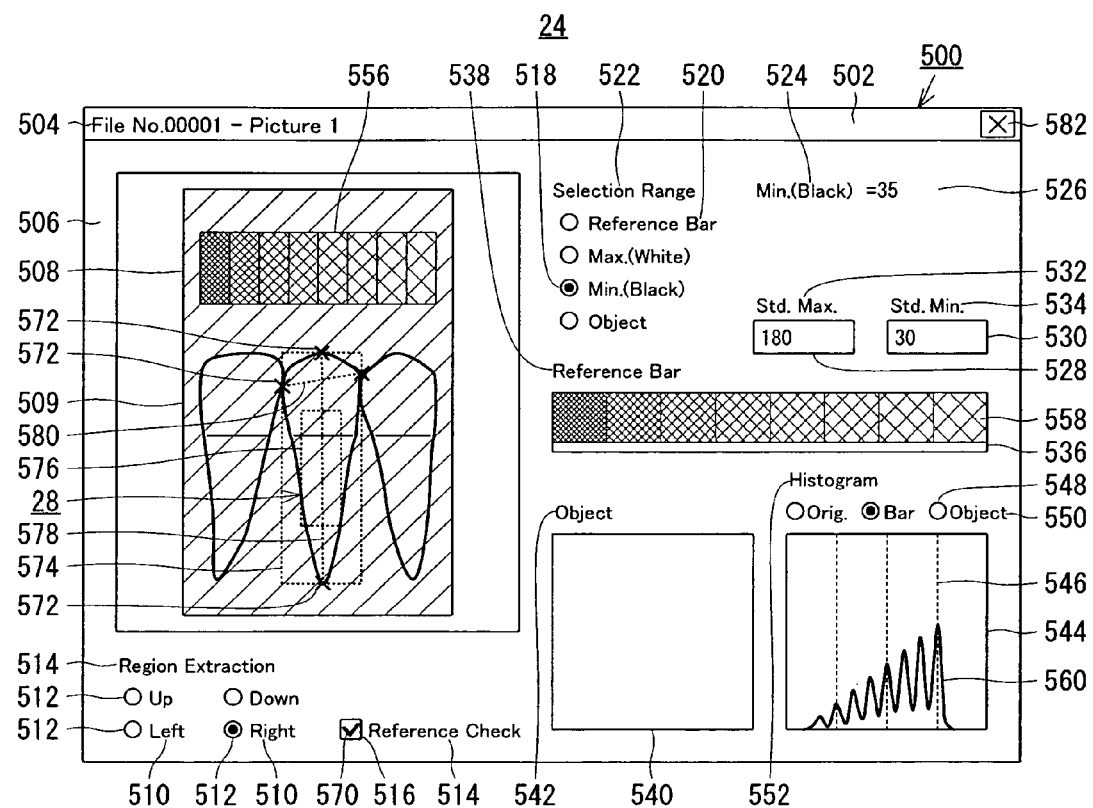
FIG. 36 is an illustration of a subsidiary picture different from the one shown in FIG. 35.

Similarly, by clicking the radio buttons 512 with the legends of "Down", "Left" and "Right", the portions on the X-ray picture 509 corresponding to the lowermost, leftmost and rightmost portions of the first premolar 28 are marked 572, respectively, as shown in FIG. 36. When the four marks 572 are attached to the uppermost, lowermost, leftmost and rightmost portions, rectangle-forming marking lines 574 are automatically drawn, with respective ones of the four marks 572 located on the four sides of the rectangle 574. Further, additional marking lines 576 forming a rectangle having a size one-half that of the rectangle 574 are drawn in the center portion of the marking lines 574, and straight marking lines 578 and 560 each connecting the opposing two marks 572 are drawn, too.

Figure 37:
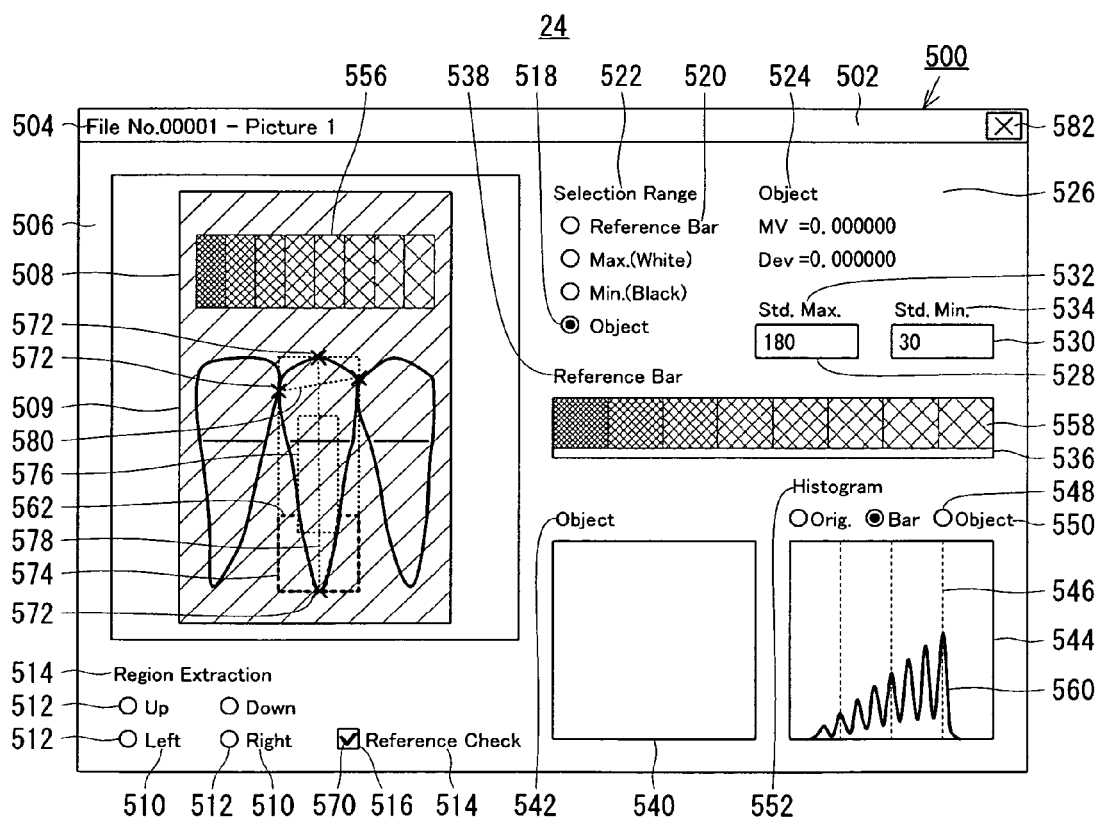
FIG. 37 is an illustration of a subsidiary picture different from the one shown in FIG. 36.

Then, as shown in FIG. 37, it becomes easy to define the evaluation object region 562 by drawing it by referencing to the lines 574-580, i.e. by selecting the start point, the respective apexes, and the end point, and, thus, the evaluation region 562 can have a fixed shape and size. It should be noted that the order in which the radio buttons 512 are clicked is arbitrary, and, also the locations of the marks 572 can be changed as desired. When the check 570 is removed (i.e. when the check box 516 is clicked again), the marks 572 and the marking lines 574-580 disappear.

Figure 38:
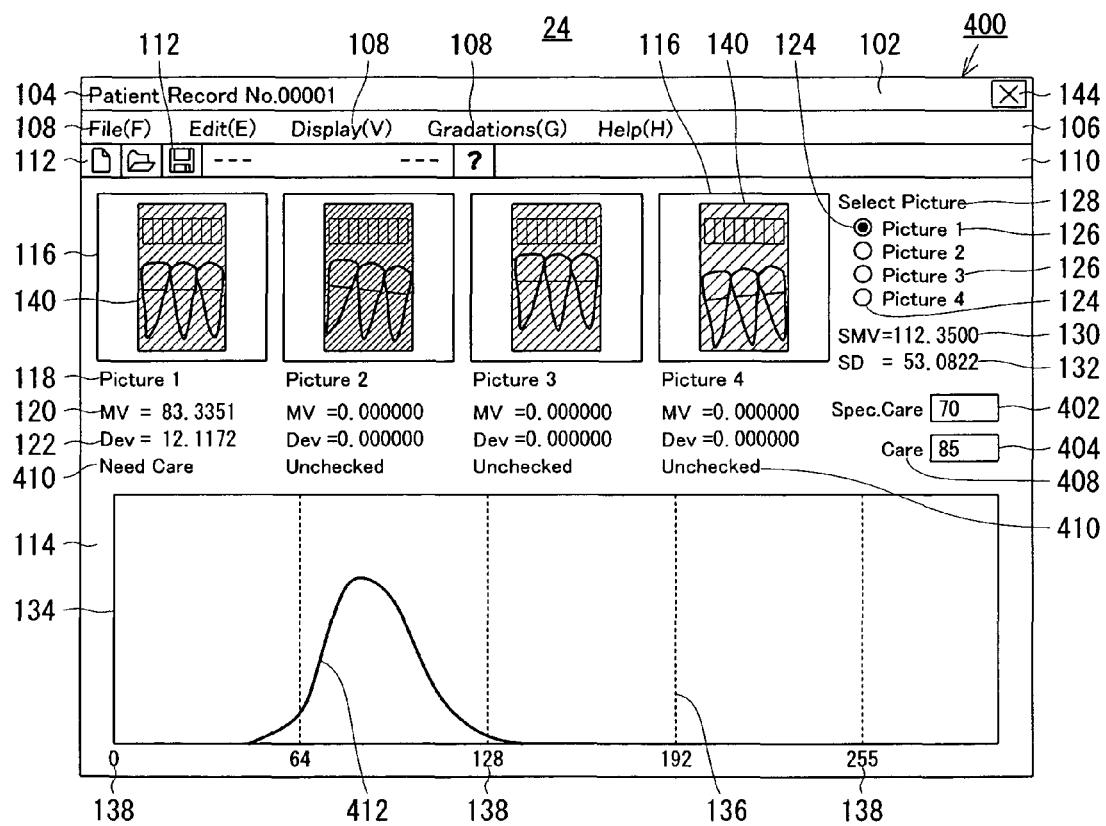
FIG. 38 is an illustration of a main picture different from the one shown in FIG. 26.

When the closing button 582 at the right-side end of the title bar 502 is clicked after the correction procedure on the subsidiary picture 500 is completed, the picture on the display 24 returns to the main picture 100 shown in FIG. 38.

In the main picture 100, the corrected mean value Mo' and the corrected deviation Do' are displayed by means of the letter groups 120 and 122 below the picture box 116 of "Picture 1", and the standard mean value SMb and the standard deviation SDb are displayed by means of the letter groups 130 and 132 in the right-side portion of the main picture 100. The diagnosis made on the basis of the corrected mean value Mo' is displayed beside the letter group 410, "Check". In the illustrated example, the corrected mean value Mo' (=83.3351) is larger than the value (=70) in the edit box 402 with the legend "Need Special Care" attached to it, but is smaller than the value in the edit box 404 with the legend "Need Care" attached to it, and, therefore, the result of "Need Care" is displayed to indicate the possibility of osteopenia. If the corrected mean value Mo' is smaller than the value in the edit box 402 with the legend "Need Special Care", the phrase "Need Special Care" is displayed, which indicates, as the diagnosis, the probability of osteoporosis. If the corrected mean value Mo' is larger than the value in the edit box 404 with the legend "Need Care" attached to it, the diagnosis of "Normal" is displayed.

Further, a curve 412 according to the corrected frequency Ho'[x] is displayed in the histogram display area 134. The curve 412 is similar to the curve 560 shown in FIG. 34. Although not known from FIG. 38, the X-ray picture 140 according to the corrected brightness Y'[i,j], i.e. the corrected X-ray picture 140, is displayed in the picture box 116 for "Picture 1".

Figure 39:
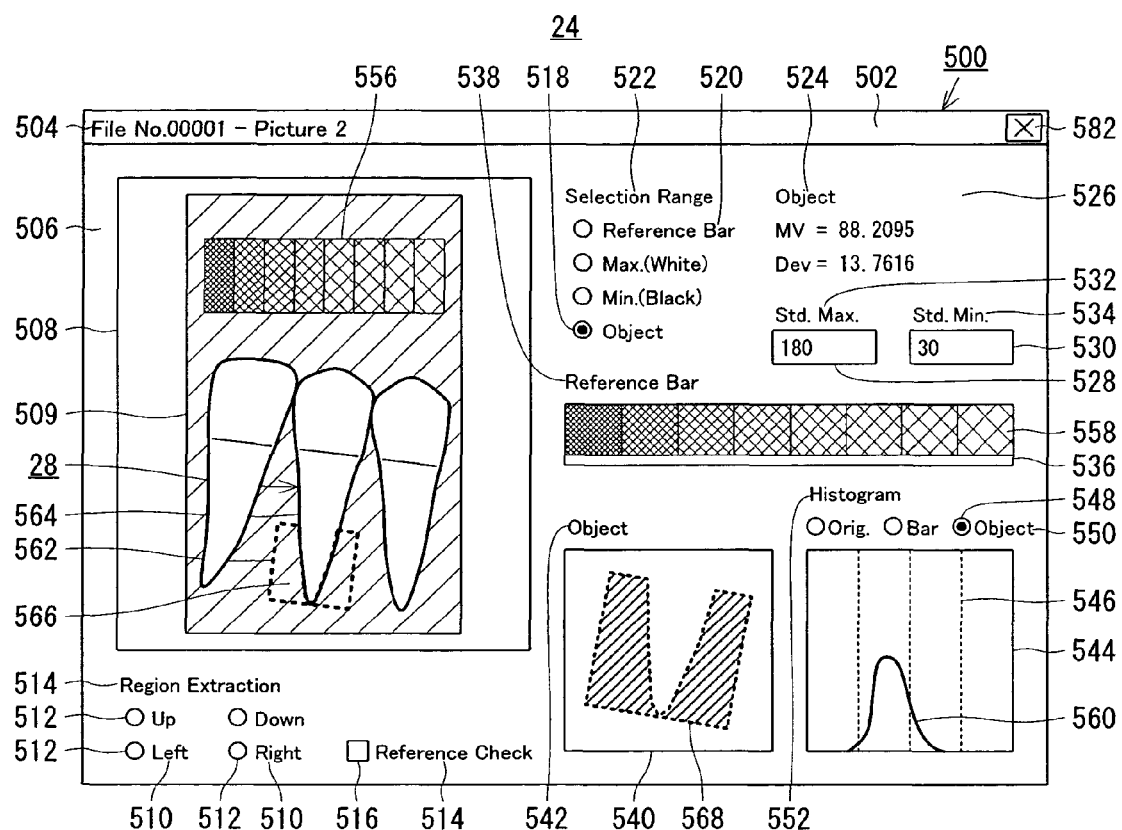
FIG. 39 is an illustration of a subsidiary picture different from the one shown in FIG. 37.

Similarly, the subsidiary picture 500 is displayed for each of the other "Picture A", namely, "Picture 2", "Picture 3", and "Picture 4", and, upon selection of the reference bar region 554 and the evaluation object region 562 on the displayed subsidiary picture 500, the subsidiary picture 500 changes to the one shown in FIG. 39, which, in the illustrated example, is the subsidiary picture 500 for "Picture 2".

On the subsidiary picture 500 for a picture other than "Picture 1", the correction procedure is partly different from the one for "Picture 1". When the reference bar region 554 is selected, the uncorrected frequency Hb[x], mean brightness value Mb and brightness deviation Db of the reference bar region 554 are calculated, using the above-described Expressions 1, 2 and 3. The results Hb[x], Mb and Db are recorded in the table 600, and the brightness Y[i,j] of the X-ray picture 140 (its enlarged picture 509) is corrected in accordance with these uncorrected frequency Hb[x], mean brightness value Mb and brightness deviation Db. Specifically, the corrected brightness Y'[i,j] is determined, using the following Expression 16, which is similar to Expression 7.

$$Y'[i, j] = \frac{SDb}{Db}(Y[i, j] - Mb) + SMb \qquad \text{[Expression 16]}$$

In other words, for the "Picture A" other than "Picture 1", the brightness correction is made based on the corrected brightness Yb'[i,j] of the reference bar region 554 of "Picture 1". The corrections following the brightness correction are carried out in manners similar to those for "Picture 1".

Figure 40:
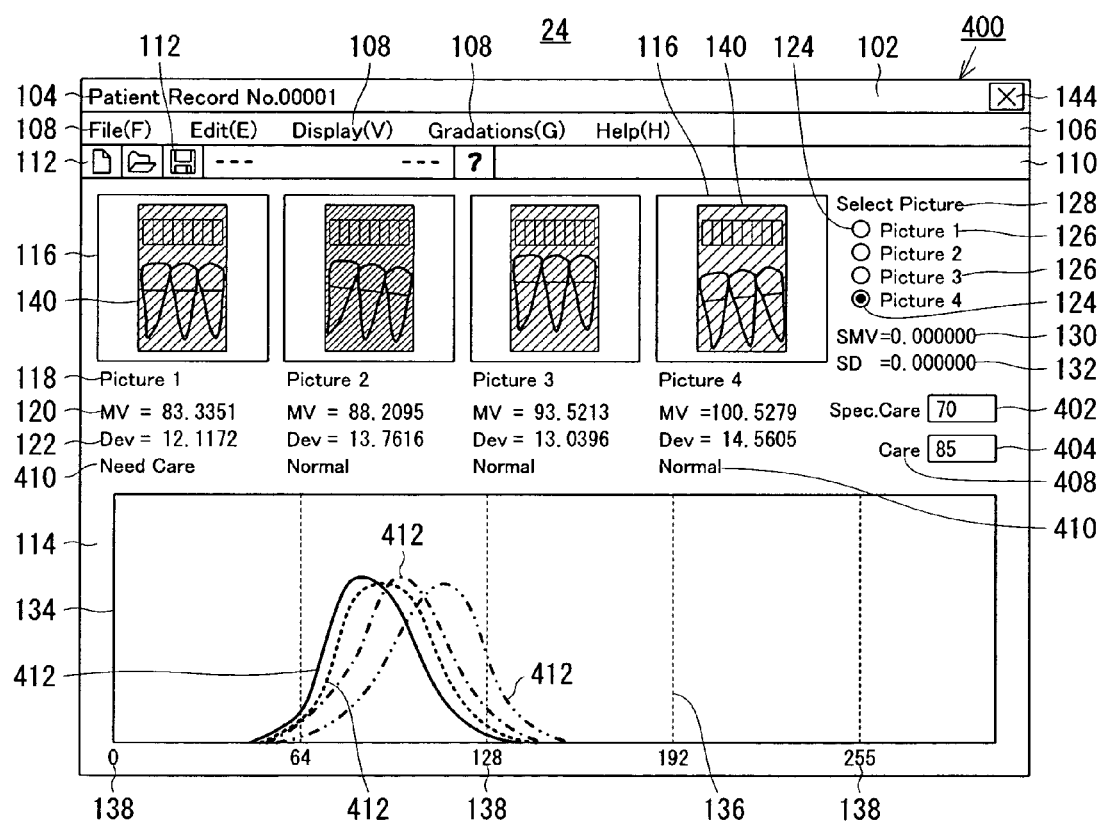
FIG. 40 is an illustration of a main picture different from the one shown in FIG. 38.

When the corrections of all the pictures, "Picture A", are completed on the respective subsidiary pictures 500, and the display is returned to the main picture 400 as shown in FIG. 40.

More specifically, the corrected mean value Mo' and corrected deviation Do' of each "Picture A" are displayed in the form of letter groups 120 and 122 below the picture box 116 for that picture, and the diagnosis made based on the corrected mean value Mo' is displayed in the form of letter group 410. Further, the X-ray picture in the picture box 116 is modified according to the corrected brightness Y'[i,j], and the modified picture is displayed. Also, four curves 412 according to the corrected frequencies Ho'[x] of the respective ones of "Picture A" are displayed in different colors in the histogram display area 134.

As described above, according to the second embodiment, the brightness Y[i,j] of "Picture 1" is corrected on the basis of fixed standards, namely, the standard maximum value Ysmax and standard minimum value Ysmin. Then, based on the corrected brightness Yb'[i,j] of the reference bar region 554 of "Picture 1" as corrected based on the fixed standards, the brightness correction is carried out for another "Picture A", i.e. each of "Picture 2", "Picture 3" and "Picture 4". This means that the brightness correction for each of "Picture 2", "Picture 3" and "Picture 4" is done also on the basis of the fixed standards. Thus, the bone mineral density can be judged from the corrected brightness Y'[i,j] or, more strictly, the corrected mean value Mo', of each "Picture A". In addition, since the result of judgment is displayed on the main picture 400 (in the form of the letter group 410), the patient himself or herself can easily know his or her bone mineral density. The result of judgment can, of course, be printed out and/or recorded on a record medium.

What is claimed is:

1. A bone mineral density evaluation system for evaluating a bone mineral density from an X-ray picture of a mandible, said X-ray picture containing a picture of an artificial reference specimen disposed beside a picture of said mandible, said X-ray picture resulting from x-raying said artificial reference specimen disposed in such a position that said picture of said artificial reference specimen is positioned beside said picture of said mandible in said X-ray picture, said system comprising:

detecting means for detecting a brightness of a particular portion of said picture of said artificial reference specimen;
   correcting means for correcting the brightness of said X-ray picture so as to make the brightness of said particular portion of said picture of said artificial reference specimen as detected by said detecting means equal to a preset standard value; and
   evaluating means for evaluating the bone mineral density on the basis of the corrected brightness of said X-ray picture as corrected by said correcting means;
   said evaluating means making evaluation on the basis of the corrected brightness of a particular region of said picture of said mandible in said X-ray picture;
   said particular region including a region corresponding to an alveolar bone portion around a first premolar.

2. The bone mineral density evaluation system according to claim 1 wherein said evaluating means includes display means for displaying said corrected brightness of said particular region of the picture of said mandible in the form of histogram.

3. The bone mineral density evaluation system according to claim 1 wherein said evaluating means includes judging means for judging a level of said bone mineral density on the basis of said corrected brightness.

4. The bone mineral density evaluation system according to claim 1, further comprising output means for providing together a plurality of evaluation results provided by said evaluating means for respective ones of a plurality of X-ray pictures.

5. A bone mineral density evaluation system for evaluating a bone mineral density from an X-ray picture of a mandible, said X-ray picture containing a picture of an artificial reference specimen disposed beside a picture of said mandible, said X-ray picture resulting from x-raying said artificial reference specimen disposed in such a position that said picture of said artificial reference specimen is positioned beside said picture of said mandible in said X-ray picture, a brightness of said picture of said artificial reference specimen varying from portion to portion, said system comprising:

detecting means for detecting an average value and a deviation of the brightness of said picture of said artificial reference specimen;
   correcting means for correcting the brightness of said X-ray picture so as to make the-average value and the deviation as detected by said detecting means equal to a preset standard average value and a preset standard deviation, respectively; and
   evaluating means for evaluating the bone mineral density on the basis of the corrected brightness of said X-ray picture as corrected by said correcting means,
   said evaluating means making evaluation on the basis of the corrected brightness of a particular region of said picture of said mandible in said X-ray picture,
   said particular region including a region corresponding to an alveolar bone portion around a first premolar.

6. The bone mineral density evaluation system according to claim 5 wherein said evaluating means includes display means for displaying said corrected brightness of said particular region of the picture of said mandible in the form of histogram.

7. The bone mineral density evaluation system according to claim 5 wherein said evaluating means includes judging means for judging a level of said bone mineral density on the basis of said corrected brightness.

8. The bone mineral density evaluation system according to claim 5, further comprising output means for providing together a plurality of evaluation results provided by said evaluating means for respective ones of a plurality of X-ray pictures.

9. The bone mineral density evaluation system according to claim 5, wherein said artificial reference specimen is an aluminum block.

10. The bone mineral density evaluation system according to claim 9, wherein said aluminum block has a stepped structure.

11. The bone mineral density evaluation system according to claim 5, wherein said artificial reference specimen has a stepped structure.

12. The bone mineral density evaluation system according to claim 1, wherein said artificial reference specimen is an aluminum block.

13. The bone mineral density evaluation system according to claim 12, wherein said aluminum block has a stepped structure.

14. The bone mineral density evaluation system according to claim 1, wherein said artificial reference specimen has a stepped structure.

* * * * *